US008835163B2

(12) United States Patent
Zhao et al.

(10) Patent No.: US 8,835,163 B2
(45) Date of Patent: *Sep. 16, 2014

(54) EMBRYONIC-LIKE STEM CELLS DERIVED FROM ADULT HUMAN PERIPHERAL BLOOD AND METHODS OF USE

(75) Inventors: Yong Zhao, Lisle, IL (US); Theodore Mazzone, Wilmette, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 638 days.

This patent is subject to a terminal disclaimer.

(21) Appl. No.: 12/445,505

(22) PCT Filed: Oct. 18, 2007

(86) PCT No.: PCT/US2007/022260
§ 371 (c)(1),
(2), (4) Date: Jun. 22, 2009

(87) PCT Pub. No.: WO2008/048671
PCT Pub. Date: Apr. 24, 2008

(65) Prior Publication Data
US 2010/0129440 A1    May 27, 2010

Related U.S. Application Data

(60) Provisional application No. 60/852,901, filed on Oct. 18, 2001, provisional application No. 60/926,846, filed on Apr. 30, 2007.

(51) Int. Cl.
| | |
|---|---|
| *C12N 5/10* | (2006.01) |
| *A61K 35/14* | (2006.01) |
| *C12N 5/071* | (2010.01) |
| *A61K 35/54* | (2006.01) |
| *C12N 5/074* | (2010.01) |
| *C12N 5/078* | (2010.01) |
| *A61K 35/39* | (2006.01) |
| *A61K 35/12* | (2006.01) |

(52) U.S. Cl.
CPC .......... *C12N 5/0607* (2013.01); *C12N 2501/22* (2013.01); *A61K 2035/122* (2013.01); *C12N 2500/34* (2013.01); *A61K 35/17* (2013.01); *C12N 2506/03* (2013.01); *C12N 5/0676* (2013.01); *A61K 35/545* (2013.01); *C12N 2501/335* (2013.01); *C12N 5/0634* (2013.01); *A61K 35/39* (2013.01)
USPC ............ 435/325; 435/363; 435/366; 435/372

(58) Field of Classification Search
None
See application file for complete search history.

(56) References Cited

U.S. PATENT DOCUMENTS

| | | | |
|---|---|---|---|
| 4,281,061 | A | 7/1981 | Zuk et al. |
| 4,362,155 | A | 12/1982 | Skurkovich |
| 4,614,513 | A | 9/1986 | Bensinger |
| 4,959,313 | A | 9/1990 | Taketo |
| 5,286,632 | A | 2/1994 | Jones |
| 5,320,962 | A | 6/1994 | Stiles et al. |
| 5,342,761 | A | 8/1994 | MacLeod |
| 5,618,698 | A | 4/1997 | Lin |
| 5,639,275 | A | 6/1997 | Baetge et al. |
| 5,670,488 | A | 9/1997 | Gregory et al. |
| 5,733,541 | A | 3/1998 | Taichman et al. |
| 5,981,225 | A | 11/1999 | Kochanek et al. |
| 6,258,354 | B1 | 7/2001 | Greenberger |
| 6,274,378 | B1 | 8/2001 | Steinman et al. |
| 6,309,883 | B1 | 10/2001 | Minshull et al. |
| 6,392,118 | B1 | 5/2002 | Hammang et al. |
| 6,465,247 | B1 | 10/2002 | Weissman et al. |
| 6,503,498 | B1 | 1/2003 | Gerard et al. |
| 6,534,055 | B1 | 3/2003 | June et al. |
| 6,544,780 | B1 | 4/2003 | Wang |
| 6,667,391 | B1 | 12/2003 | Drmanac et al. |
| 6,783,964 | B2 | 8/2004 | Opara |
| 7,045,148 | B2 | 5/2006 | Hariri |
| 2002/0028510 | A1 | 3/2002 | Sanberg et al. |
| 2002/0160510 | A1 | 10/2002 | Hariri |
| 2002/0182728 | A1 | 12/2002 | Ramiya et al. |

(Continued)

FOREIGN PATENT DOCUMENTS

| | | |
|---|---|---|
| WO | 90/11354 A1 | 10/1990 |
| WO | 92/03917 A1 | 3/1992 |
| WO | 9218615 A1 | 10/1992 |
| WO | 93/04169 A1 | 3/1993 |
| WO | 9312805 A1 | 7/1993 |
| WO | 95/17911 A1 | 7/1995 |
| WO | 9920741 A1 | 4/1999 |
| WO | 9961584 A1 | 12/1999 |
| WO | 0162895 A2 | 8/2001 |
| WO | WO 02/076501 | 10/2002 |

(Continued)

OTHER PUBLICATIONS

Price et al. Stem Cells Dev 2006;15:507-22.*

(Continued)

*Primary Examiner* — Janice Li
(74) *Attorney, Agent, or Firm* — Weisun Rao; Greenberg Traurig, LLP

(57) ABSTRACT

The present invention is related generally to embryonic-like stem cells isolated from adult human peripheral blood, designated herein as peripheral blood-stem cells (PB-SC), which display the characteristics of embryonic stem cells and hematopoietic cells. These cells have the capability of proliferation and are able to differentiate to other types of cells. These cells are, therefore, suitable for use in stem cell-based therapies, particularly autologous stem cell therapies, for the treatment of various diseases such as neurodegenerative diseases, autoimmune diseases, diabetes, spinal cord damage, multiple sclerosis, cardiovascular disease, stroke and birth defects.

35 Claims, 13 Drawing Sheets

(56) References Cited

U.S. PATENT DOCUMENTS

| | | |
|---|---|---|
| 2003/0180269 A1 | 9/2003 | Hariri |
| 2003/0235909 A1 | 12/2003 | Hariri et al. |
| 2004/0022403 A1 | 2/2004 | Ballisager et al. |
| 2004/0028658 A1 | 2/2004 | Faustman |
| 2004/0028660 A1 | 2/2004 | Hariri et al. |
| 2004/0224403 A1 | 11/2004 | Bhatia |
| 2005/0118715 A1 | 6/2005 | Hariri et al. |
| 2005/0148034 A1 | 7/2005 | Hariri et al. |
| 2006/0078993 A1 | 4/2006 | Phan et al. |
| 2006/0147426 A1 | 7/2006 | Schiller et al. |
| 2007/0059824 A1 | 3/2007 | Zhao et al. |
| 2008/0159998 A1 | 7/2008 | Ichim |
| 2008/0293135 A1 | 11/2008 | Orr et al. |
| 2009/0175832 A1* | 7/2009 | Zhao et al. .......... 424/93.7 |

FOREIGN PATENT DOCUMENTS

| | | |
|---|---|---|
| WO | 02097067 A1 | 12/2002 |
| WO | WO 03/055989 | 7/2003 |
| WO | WO 03/068937 | 8/2003 |
| WO | 0383092 A1 | 10/2003 |
| WO | WO 2006/044842 | 4/2006 |
| WO | WO 2007/044314 | 4/2007 |
| WO | WO 2008/048671 | 4/2008 |

OTHER PUBLICATIONS

Rutella et al. J Immunol 2003;171:2977-88.*
Galic et al. PNAS 2006;103:11742-7.*
Abuljadayel et al. Curr Med Res Opin 2003;19:355-75.*
Xiao et al, Stem Cell Develop 2005;14:722-33.*
GeneTex, Inc. 2010.*
De Mulder et al. Clin Exp Immunol 1983;54:681-8.*
Preffer et al. Stem Cells 2002;20:417-27.*
Carlin et al. Reprod Biol Endocrinol Feb. 2006;4:8,1-13.*
Michalopoulos, G.K. et al., "Liver Regeneration", Science, vol. 276, p. 60, 1997.
Rehman, J. et al., "Peripheral Blood Endotherlial Progenitor Cells Are Derived From Monocyte/Macrophages and Secrete Angiogenic Growth Factors", Circulation, vol. 107, pp. 1164-1169, 2003.
International Search Report for PCT/US2006/038524, dated Jun. 25, 2007 (2 pages).
Written Opinion of International Searching Authority for PCT/US2006/038524, dated Jun. 25, 2007 (4 pages).
International Preliminary Report on Patentability for PCT/US2007/022260, dated Apr. 30, 2009 (9 pages).
International Search Report for PCT/US2007/022260, dated Mar. 17, 2008 (5 pages).
Written Opinion of International Searching Authority for PCT/US2007/022260, dated Mar. 17, 2008 (7 pages).
Written Opinion of International Searching Authority for PCT/US2010/059522, dated Apr. 28, 2011 (5 pages).
Extended European Search Report for EP 06825367.3, dated May 12, 2009 (10 pages).
Bjorklund, A. et al., "Cell Replacement Therapies for Central Nervous System Disorders", Nature Neurosciences, vol. 3, pp. 537-544, 2000.
Buzanska, L. et al., "Human Cord Blood-Derived Cells Attain Neuronal and Glial Features In Vitro", J. Cell Sci., vol. 115, pp. 2131-2138, 2002.
Carpenter, G., "EGF: New Tricks for an Old Growth Factor", Current Opinion in Cell Biology, vol. 5, pp. 261-264, 1993.
Chang, C-J et al., "Placenta-Derived Multipotent Cells Exhibit Immunosuppressive Properties That Are Enhanced in the Presence of Interferon-?", Stem Cells, vol. 24, pp. 2466-2477, 2006.
Djouad, F. et al., "Immunosuppressive Effect of Mesenchymal Stem Cells Favors Tumor Growth in Allogeneic Animals", Blood, vol. 102, pp. 3837-3844, 2003.
Donovan, P.J. et al., "The End of the Beginning for Pluripotent Stem Cells", Nature, vol. 414, pp. 92-97, 2001.
Ellis, M.H. et al., "The Regulation of Megakaryocytopoiesis", Blood Reviews, vol. 9, pp. 1-6, 1995.
Encinas, M. et al., "Sequential Treatment of SH-SY5Y Cells With Retinoic Acid and Brain-Derived Neurotrophic Factor Gives Rise to Fully Differentiated, Neurotrophic Factor-Dependent, Human Neuron-Like Cells", Journal of Neurochemistry, vol. 75, pp. 991-1003, 2000.
Gluckman, E. et al., "Hematopoietic Reconstitution in a Patient With Fanconi's Anemia B Means of Umbilical-Cord Blood From an HLA-Identical Sibling", NEJM, vol. 321, pp. 1174-1178, 1989.
Gordon, S. et al., "Molecular Immunobiology of Macrophages: Recent Progress", Current Opinion in Immunology, vol. 7, pp. 24-33, 1995.
Gotze, K. et al., "Flt3high and Flt3low CD34+ Progenitor Cells Isolated From Human Bone Marrow Are Functionally Distinct", Blood, vol. 91, pp. 1947-1958, 1998.
Grage-Griebenow, E. et al., "Heterogeneity of Human Peripheral Blood Monocyte Subsets", Journal of Leukocyte Biology, vol. 69, pp. 11-20, 2001.
Griffith, L. G. et al., "Tissue Engineering-Current Challenges and Expanding Opportunities", Science, vol. 295, pp. 1009-1014, 2002.
Gu, D. et al., "Epithelial Cell Proliferation and Islet Neogenesis in IFN-g Transgenic Mice", Development, vol. 118, pp. 33-46, 1993.
Hamazaki, T. et al., "Hepatic Maturation in Differentiating Embryonic Stem Cells In Vitro", FEBS Letters, vol. 497, pp. 15-19, 2001.
Hamid, M. et al., "Comparative Functional Study of Clonal Insulin-Secreting Cells Cultured in Five Commercially Available Tissue Culture Media", Cell Transplantation, vol. 10, pp. 153-159, 2001.
Ishikawa, F. et al., "Tranplanted Human Cord Blood Cells Give Rise to Hepatocytes in Engrafted Mice", Annals NY Acad Sci., vol. 996, pp. 174-185, 2003.
Jacovina, A.T. et al., "Neuritogenesis and the Nerve Growth Factor-Induced Differentiation of PC-12 Cells Requires Annexin II-Mediated Plasmin Generation", The Journal of Biological Chemistry, vol. 276, pp. 49350-49358, 2001.
Jiang, Y. et al., "Pluripotency of Mesenchymal Stem Cells Derived From Adult Marrow", Nature, vol. 418, pp. 41-49, 2002.
Karkkainen, M. et al., "Lymphatic Endothelium: A New Frontier of Metastasis Research", Nature Cell Biology, vol. 4, pp. E2-E5, 2002.
Korbling, M. et al., "Hepatocytes and Epithelial Cells of Donor Origin in Recipients of Peripheral-Blood Stem Cells", N Engl J Med, vol. 346, pp. 738-746, 2002.
Lagasse, E. et al., "Purified Hematopoietic Stem Cells Differentiate Into Hepatocytes In Vivo", Nature Medicine, vol. 6, pp. 1229-1234, 2000.
Lederman, S. et al., "Antigen Presenting Cells Integrate Opposing Signals From CD4+ and CD8+ Regulatory T Lymphocytes to Arbitrate the Outcomes of Immune Responses", vol. 60, pp. 553-561, 1999.
Lee, O.K. et al., "Isolation of Multipotent Mesenchymal Stem Cells From umbilical Cord Blood", Blood, vol. 103, pp. 1669-1675, 2004.
Lee, M.W. et al., "Mesenchymal Stem Cells From Cryopreserved Human Umbilical Cord Blood", Biochem Biophy Res Comm, vol. 320, pp. 273-278, 2004.
Li, J. et al "The End Is Just the Beginning: Megakaryocyte Apoptosis and Platelet Release", International Journal of Hematology, vol. 74, pp. 365-374, 2001.
Lovell-Badge, R., "The Future for Stem Cell Research", Nature, vol. 414, pp. 88-91, 2001.
Lumelsky, N. et al., "Differentiation of Embryonic Stem Cells to Insulin-Secreting Structures Similar to Pancreatic Islets", Science, vol. 292, pp. 1389-1394, 2001.
McAllister, A.K., "Neurotrophins and Neuronal Differentiation in the Central Nervous System", CMLS, Cell. Mol. Life Sci., vol. 58, pp. 1054-1060, 2001.
Nakabo, Y. et al., "Lysis of Leukemic Cells by Human Macrophages: Inhibition by 4-(2-Aminoethyl)-Benzenesulfonyl Fluoride (AEBSF), A Serine Protease Inhibitor", Journal of Leukocyte, vol. 60, pp. 328-336, 1996.
Orlic, D. et al., "Bone Marrow Cells Regenerate Infarcted Myocardium", Nature, vol. 410, pp. 701-705, 2001.
Pittenger, M.F. et al., "Multilineage Potential of Adult Human Mesenchymal Stem Cells", Nature, vol. 284, pp. 143-147, 1999.

(56) References Cited

OTHER PUBLICATIONS

Randall, T.D. et al., "Characterization of a Population of Cells in the Bone Marrow That Phenotypically Mimics Hematopoietic Stem Cells: Resting Stem Cells or Mystery Population", Stem Cells, vol. 16, pp. 38-48, 1998.
Ruck, P. et al., "Hepatic Stem-Like Cells in Hepatoblastoma: Expression of Cytokeratin 7, Albumin and Oval Cell Associated Antigens Detected by OV-1 and OV-6", Histopathology, vol. 31, pp. 324-329, 1997.
Ryffel, B. et al., "Differentiation of Human T-Lymphoid Leukemia Cells Into Cells That Have a Suppressor Phenotype Is Induced by Phorbol 12-Myristate 13-Acetate", Proc. Natl. Acad. Sci. USA, vol. 79, pp. 7336-7340, 1982.
Schmidt, C. et al., "Scatter Factor/Hepatocyte Growth Factor is Essential for Liver Development", Nature, vol. 373, pp. 699-702, 1995.
Schuit, F. et al., "Metabolic Fate of Glucose in Purified Islet Cells", The Journal of Biological Chemistry, vol. 272, pp. 18572-18579, 1997.
Sorg, R.V. et al., "Phenotypic and Functional Comparison of Monocytes From Cord Blood and Granulocyte Colony-Stimulating Factor-Mobilized Apheresis Product", Experimental Hematology, vol. 29, pp. 1289-1294, 2001.
Swanson, J.A. et al., "Cellular Dimensions Affecting the Nucleocytoplasmic volume Ratio", The Journal of Cell Biology, vol. 115, pp. 941-948, 1991.
Terada, N. et al., "Bone Marrow Cells Adopt the Phenotype of Other Cells by Spontoneous Cell Fusion", Nature, vol. 416, pp. 542-545, 2002.
Tontonoz, P. et al., "PPAR? Promotes Monocyte/Macrophage Differentiation and Uptake of Oxidized LDL", Cell, v. 93, pp. 241-252, 1998.
Tseng, S.C. et al., "Correlation of Specific Keratins With Different types of Epithelial Differentiation: Monoclonal Antibody Studies", Cell, vol. 30, pp. 361-372, 1982.
Vadiveloo, P.K., "Macrophages-Proliferation, Activation, and Cell Cycle Proteins", Journal of Leukocyte Biology, vol. 66, pp. 579-582, 1999.
Weissman, "Stem Cells—Scientific, Medical, and Political Issues", N. Engl J Med, vol. 346, pp. 1576-1579, 2002.
Ying, Q-L et al., "Changing Potency by Spontaneous Fusion", Nature, vol. 416, pp. 545-548, 2002.
Zhou, L-J et al., "CD14+ Blood Monocytes Can Differentiate Into functionally Mature CD83 Dendritic Cells", Proc. Natl. Acad. Sci. USA, vol. 93, pp. 2588-2592, 1996.
Zhu, X. et al., "Severe Block in Processing of Proinsulin to Insulin Accompanied by Elevation of Des-64,65 Proinsulin Intermediates in Islets of Mice Lacking Prohormone Convertase 1/3", PNAS, vol. 99, pp. 10299-10304, 2002.
Zucker-Franklin, D., Megakaryocyte and Platelet Structure in Thrombocytopoiesis: The Effect of Cytokines, Stem Cells, vol. 14 (Suppl 1), pp. 1-17, 1996.
Adamson, "Cord Blood Stem Cell Banking and Transplantation. Hematopoietic Stem Cells", Stem Cells, vol. 15, Suppl. 1, pp. 57-61, 1997.
Birkmann, J. et al., "Effects of Recombinant Human Thrombopoietin Alone and in Combination With Erythropietin and Early-Acting Cytokines on Human Mobilized Purified CD34 Progenitor Cells Cultured in Serum-Depleted Medium", Stem Cells, vol. 15, pp. 18-32, 1997.
Zhao, Y. et al., "Human Unbilical Cord Blood-Derived F-Macrophages Retain Pluripotentially After Thrombopoietin Expansion", Experimental Cell Research, vol. 310, pp. 311-318, 2005.
Zhao, Y. et al., "A Human Peripheral Blood Monocyte-Derived Subset Acts As Pluripotent Stem Cells", PNAS, vol. 100, No. 5, pp. 2426-2431, 2003.
Brolen et al., Signals from the embryonic mouse pancreas induce differentiation of human embryonic stem cells into insulin-producing beta-cell-like cells. Diabetes. Oct. 2005;54(10):2867-74.

Cai et al., Microencapsulated hepatocytes for bioartificial liver support. Artif Organs. Oct. 1988;12(5):388-93.
Chang, TM, Artificial liver support based on artificial cells with emphasis on encapsulated hepatocytes. Artif Organs. Feb. 1992;16(1):71-4.
Chang et al., The in vivo delivery of heterologous proteins by microencapsulated recombinant cells. Trends Biotechnol. Feb. 1999;17(2):78-83.
Choileain et al., Regulatory T-cells and autoimmunity. J. Surg Res. Jan. 2006;130(1):124-35. Epub Sep. 8, 2005.
Cicuttini et al., Characterization of CD34+HLA-DR-CD38+ and CD34+HLA-DR-CD38− progenitor cells from human umbilical cord blood. Growth Factors. 1994;10(2):127-34.
Craig et al., CD45 isoform expression on human haemopoietic cells at different stages of development. Br J Haematol. Sep. 1994;88(1):24-30.
da Silva Meirelles et al., Mesenchymal stem cells reside in virtually all post-natal organs and tissues. J Cell Sci. Jun. 1, 2006;119(Pt 11):2204-13. Epub May 9, 2006.
Del Prete et al., Human IL-10 is produced by both type 1 helper (Th1) and type 2 helper (Th2) T cell clones and inhibits their antigen-specific proliferation and cytokine production. J Immunol. Jan. 15, 1993;150(2):353-60.
Dennis et al., 'Ethical' routes to stem cells highlight political divide. Nature. Oct. 20, 2005;437(7062):1076-7.
Docherty et al., Carboxypeptidase activity in the insulin secretory granule. FEBS Lett. Oct. 3, 1983;162(1):137-41.
Drukker et al., Characterization of the expression of MHC proteins in human embryonic stem cells. Proc Natl Acad Sci U S A. Jul. 23, 2002;99(15):9864-9. Epub Jul. 11, 2002.
Edlund, H, Pancreatic organogenesis—developmental mechanisms and implications for therapy. Nat Rev Genet. Jul. 2002;3(7):524-32.
European Office Action for Application No. 06825367.3, dated Jul. 5, 2012. (4 pages).
Evans, M., Ethical sourcing of human embryonic stem cells—rational solutions? Nat Rev Mol Cell Biol. Aug. 2005;6(8):663-7.
Gang et al., In vitro mesengenic potential of human umbilical cord blood-derived mesenchymal stem cells. Biochem Biophys Res Commun. Aug. 13, 2004;321(1):102-8.
Grove et al., Plasticity of bone marrow-derived stem cells. Stem Cells. 2004;22(4):487-500.
Hadkar et al., Carboxypeptidase-mediated enhancement of nitric oxide production in rat lungs and microvascular endothelial cells. Am J Physiol Lung Cell Mol Physiol. Jul. 2004;287(1):L35-45. Epub Feb. 20, 2004.
Hawrylowicz et al., Potential role of interleukin-10-secreting regulatory T cells in allergy and asthma. Nat Rev Immunol. Apr. 2005;5(4):271-83.
Hawrylowicz, CM, Regulatory T cells and IL-10 in allergic inflammation. J Exp Med. Dec. 5, 2005;202(11):1459-63.
Hayek et al., Experimental transplantation of human fetal and adult pancreatic islets. J Clin Endocrinol Metab. Aug. 1997;82(8):2471-5.
Hoffman et al., Characterization and culture of human embryonic stem cells. Nat Biotechnol. Jun. 2005;23(6):699-708.
Hori et al., Growth inhibitors promote differentation of insulin-producing tissue from embryonic stem cells. Proc Natl Acad Sci U S A. Dec. 10, 2002;99(25):16105-10. Epub Nov. 19, 2002.
Hori et al., Differentiation of insulin-producing cells from human neural progenitor cells. PLoS Med. Apr. 2005;2(4):e103. Epub Apr. 26, 2005.
Hussain et al., Stem-cell therapy for diabetes mellitus. Lancet. Jul. 10-16, 2004;364(9429):203-5.
Ianus et al., In vivo derivation of glucose-competent pancreatic endocrine cells from bone marrow without evidence of cell fusion. J Clin Invest. Mar. 2003;111(6):843-50.
Ingram et al., Identification of a novel hierarchy of endothelial progenitor cells using human peripheral and umbilical cord blood. Blood. Nov. 1, 2004;104(9):2752-60, Epub Jun. 29, 2004.
in't Anker, Hematologica, 2003, vol. 88, pp. 845-852.
International Preliminary Report on Patentability for Application No. PCT/US2010/059522, dated Jun. 21, 2012 (7 pages).

(56) References Cited

OTHER PUBLICATIONS

Kayali et al., The stromal cell-derived factor-1alpha/CXRXR4 ligand-receptor axis is critical for progenitor survival and migration in the pancreas. J Cell Biol. Nov. 24, 2003;163(4):859-69.
Klimanskaya et al., Human embryonic stem cells derived without feeder cells. Lancet. May 7-13, 2005;365(9471):1636-41.
Kogler et al., A new human somatic stem cell from placental cord blood with intrinsic pluripotent differentiation potential. J Exp Med. Jul. 19, 2004;200(2):123-35.
Kuwana et al., Human circulating CD14+ monocytes as a source of progenitors that exhibits mesenchymal cell differentiation. J Leukoc Biol. Nov. 2003;74(5):833-45. Epub Jul. 22, 2003.
Lansdorp et al., Long-term erythropoiesis from constant numbers of CD34+ cells in serum-free cultures initiated with highly purified progenitor cells from human bone marrow. J Exp Med. Jun. 1, 1992;175(6):1501-9.
Lapidot et al., How do stem cells find their way home? Blood. Sep. 15, 2005;106(6):1901-10. Epub May 12, 2005.
Lechner et al., No evidence for significant transdifferentation of bone marrow into pancreatic beta-cells in vivo. Diabetes. Mar. 2004;53(3):616-23.
Lee, Blood, 2004, vol. 103, pp. 1669-1675.
Lee, Intl J. Hemat, 2005, vol. 81, pp. 126-130.
Mareschi, Hematologica, 2001, vol. 86, pp. 1099-1100.
Matsuoka et al., The MafA transcription factor appears to be responsible for tissue-specific expression of insulin. Proc Natl Acad Sci U S A. Mar. 2, 2004, 101(9):2930-3. Epub Feb. 18, 2004.
Matthew et al., Microencapsulated hepatocytes. Prospects for extracorporeal liver support. ASAIO Trans. Jul.-Sep. 1991;37(3):M328-30.
McGuckin et al., Production of stem cells with embryonic characteristics from human umbilical cord blood. Cell Prolif. Aug. 2005;38(4):245-55.
Melton et al., Altered nuclear transfer in stem-cell research—a flawed proposal. N Engl J Med. Dec. 30, 2004;351(27):2791-2.
Miyazaki et al., Regulated expression of pdx-1 promotes in vitro differentiation of insulin-producing cells from embryonic stem cells. Diabetes. Apr. 2004;53(4):1030-7.
Moore et al, Interleukin-10. Annu Rev Immunol. 1993;11:165-90.
Mousa et al., Subcellular pathways of beta-endorphin synthesis, processing, and release from immunocytes in inflammatory pain. Endocrinology. Mar. 2004;145(3):1331-41. Epub Nov. 20, 2003.
Orkin, SH, Chipping away at the embryonic stem cell network. Cell. Sep. 23, 2005;122(6):828-30.
Paust et al., Regulatory T cells and autoimmune disease. Immunol Rev. Apr. 2005;204:195-207.
Peterson, D.A, Umbilical cord blood cells and brain stroke injury: bringing in fresh blood to address an old problem. J Clin Invest. Aug. 2004;114(3):312-4.
Randolph et al., Cd+Cd25+ regulatory T cells and their therapeutic potential. Annu Rev Med. 2006;57:381-402.
[No Author Listed] GenBank Accession No. AAO65969. Updated Mar. 24, 2003, 1 page.
[No Author Listed] GenBank Accession No. AF005058. Updated Sep. 21, 2000, 5 pages.
[No Author Listed] GenBank Accession No. CAA83435. Updated Apr. 18, 2005, 2 pages.
[No Author Listed] GenBank Accession No. CAG46675. Updated Jun. 29, 2004. 2 pages.
[No Author Listed] GenBank Accession No. CAG46893. Updated Jun. 29, 2004, 2 pages.
[No Author Listed] GenBank Accession No. EAW94647. Updated Dec. 18, 2006, 2 pages.
[No Author Listed] GenBank Accession No. M27394. Updated Jul. 15, 1993, 2 pages.
[No Author Listed]GenBank Accession No. M38690. Updated Nov. 11, 1995, 2 pages.
[No Author Listed] GenBank Accession No. NM_000222. Updated Jun. 21, 2009, 11 pages.
[No Author Listed] GenBank Accession No. NM_000632. Updated Apr. 6, 2008, 11 pages.
[No Author Listed] GenBank Accession No. NM_000887. Updated Apr. 6, 2008, 12 pages.
[No Author Listed] GenBank Accession No. NM_001769. Updated May 24, 2009, 7 pages.
[No Author Listed] GenBank Accession No. NM_002045. Updated Sep. 28, 2008, 7 pages.
[No Author Listed] GenBank Accession No. NM_002473. Updated Apr. 6, 2008, 15 pages.
[No Author Listed] GenBank Accession No. NM_002701. Updated Apr. 6, 2008, 6 pages.
[No Author Listed] GenBank Accession No. NM_002838. Updated May 10, 2009, 12 pages.
[No Author Listed] GenBank Accession No. NM_002851. Updated Jun. 7, 2009, 14 pages.
[No Author Listed] GenBank Accession No. NM_003413. Updated Dec. 21, 2008, 6 pages.
[No Author Listed] GenBank Accession No. NM_004426. Updated Feb. 1, 2009, 9 pages.
[No Author Listed] GenBank Accession No. NM_005397. Updated May 10, 2009, 9 pages.
[No Author Listed] GenBank Accession No. NM_007129. Updated May 10, 2009, 7 pages.
[No Author Listed]GenBank Accession No. NM_024504. Updated Mar. 27, 2008, 5 pages.
[No Author Listed] GenBank Accession No. NM_024865. Updated Feb. 11, 2008, 7 pages.
[No Author Listed] GenBank Accession No. NM_032805.1. Updated Feb. 10, 2008, 4 pages.
[No Author Listed] GenBank Accession No. NM_001040021. Updated Apr. 6, 2008, 6 pages.
[No Author Listed] GenBank Accession No. NP_001618. Updated Apr. 18, 2005, 2 pages.
[No Author Listed] GenBank Accession No. NP—005202. Updated Mar. 30, 2008, 4 pages.
[No Author Listed] GenBank Accession No. NP_057173.1 Updated Nov. 17, 2006, 2 pages.
[No Author Listed] GenBank Accession No. NP_079141. Updated Feb. 11, 2008, 3 pages.
[No Author Listed] GenBank Accession No. NP_116194.1. Updated Feb. 10, 2008, 2 pages.
[No Author Listed] GenBank Accession No. NP_001020329. Updated Mar. 16, 2008, 3 pages.
[No Author Listed] GenBank Accession No. P08571. Updated Dec. 4, 2007, 7 pages.
[No Author Listed] GenBank Accession No. P08575. Updated Jun. 16, 2009, 24 pages.
[No Author Listed] GenBank Accession No. P10721. Updated Jun. 16, 2009, 24 pages.
[No Author Listed] GenBank Accession No. P28906. Updated Mar. 18, 2008, 6 pages.
[No Author Listed] GenBank Accession No. Q01860. Updated Mar. 18, 2008, 5 pages.
[No Author Listed] GenBank Accession No. Z11898. Updated Apr. 18, 2005, 3 pages.
[No Author Listed] GenBank Accession No. Z31560. Updated Apr. 18, 2005, 2 pages.
Aoki et al., Derivation of functional endothelial progenitor cells from human umbilical cord blood mononuclear cells isolated by a novel cell filtration device. Stem Cells. 2004;22(6):994-1002.
Andreessen et al., Beta1 integrin deficiency impairs migration and differentiation of mouse embryonic stem cell derived neurons. Neurosci Lett. Jul. 31, 1998;251(3):165-8.
Aria, J. Exp. Med, 2002, vol. 195, pp. 1549-1563.
Baal et al., Expression of transcription factor Oct-4 and other embryonic genes in CD133 positive cells from human umbilical cord blood. Thromb Haemost. Oct. 2004;92(4):767-75.
Ballen, K.K., New trends in umbilical cord blood transplantation. Blood. May 15, 2005;105(10):3786-92. Epub Jan. 27, 2005.
Balley-Cuif et al., Induction and patterning of neuronal development, and its connection to cell cycle control. Curr Opin Neurobiol. Feb. 2003;13(1):16-25.

(56) References Cited

OTHER PUBLICATIONS

Baron, M, Induction of embryonic hematopoetic and endothelial stem/progenitor cells by hedgehog-mediated signals. Differentiation. Oct. 2001;68(4-5):175-85.
Battaglia et al., IL-10-producing T regulatory type 1 cells and oral tolerance. Ann N Y Acad Sci. Dec. 2004;1029:142-53.
Bieback et al., Critical parameters for the isolation of mesenchymal stem cells from umbilical cord blood. Stem Cells. 2004;22(4):625-34.
Bonadio et al., Localized, direct plasmid gene delivery in vivo: prolonged therapy results in reproducible tissue regeneration. Nat Med. Jul. 1999;5(7):753-9.
Bonde et al., Recent advances in hematopietic stem cell biology. Curr Opin Hematol. Nov. 2004;11(6):392-8.
Bradley et al., Stem cell medicine encounters the immune system. Nat Rev Immunol. Nov. 2002;(11):859-71.
Cairo, M. et al., "Placental And/Or Umbilical Cord Blood: An Alternative Source of Hematopoietic Stem Cells for Transplantation", *Blood*, vol. 90, No. 12, pp. 4665-4678, 1997.
Graversen, J. et al., "Molecules in Focus CD163: A Signal Receptor Scavenging Haptoglobin-Hemoglobin Complexes From Plasma", *The International Journal of Biochemistry& Cell Biology*, vol. 34, pp. 309-314, 2002.
Harris, D.T., "Experience in Autologous and Allogeneic Cord Blood Banking", *J. Hematotherapy*, vol. 5, pp. 123-138, 1996.
Holz, "New Insights Concerning the Glucose-Dependent Insulin Secretagogue Action of Glucagon-Like Peptide-1 in Pancreatic β-Cells", *Horm Metab Res*, vol. 36, pp. 787-794, 2004.
Hunnestad, J. et al., "Thrombopoietin Combined With Early-Acting Growth Factors Effectively Expands Human Hematopoietic Progenitor Cells In Vitro", *Stem Cells*, vol. 17, pp. 31-38, 1999.
Huss, R., "Isolation of Primary and Immortalized CD34— Hematopoietic and Mesenchymal Stem Cells From Various Sources", *Stem Cells*, vol. 18, pp. 1-9, 2000.
Kucia et al., "Morphological and Molecular Characterization of Novel Population of CXCR4+ SSEA-4+, Oct-4+ Very Small Embryonic-Like Cell Purified From Human Cord Blood—Preliminary Report", *Leukemia*, vol. 21, pp. 297-303, 2007.
Mayani, H, "Biology of Human Umbilical Cord Blood—Derived Hematopoietic Stem/Progenitor Cells", *Stem Cells*, vol. 16, pp. 153-165, 1998.
Rasmusson, "Immune Modulation by Mesenchymal Stem Cells", *Experimental Cell Research*, v. 312, pp. 2169-2179, 2006.
Romagnani et al., "CD14+CD34$^{low}$ Cells With Stem Cell Phenotypic and Functional Features Are the Major Source of Circulating Endothelial Progenitors", *Circulation Resarch*, v. 97, pp. 314-322, 2005.
Ruhnke et al., "Differentiation of In Vitro-Modified Human Peripheral Blood Monocytes Into Heptocylce-Like and Pancreatic Islet-Like Cells", *Gastroenterology*, v. 128, pp. 1774-1786, 2005.
Sirchia, G. et al., "Placental/Umbilical Cord Blood Transplantation", *Hemtologica*, vol. 84, pp. 738-747, 1999.
Yoshida et al., "Human Cord Blood-Derived Cells Generate insulin-Producing Cells In Vivo", *Stem Cells*, vol. 23, No. 9, pp. 1409-1416, 2005.
Zhao, Y. et al., "Identification of Stem Cells From Human Umbilical Cord Blood With Embryonic and Hematopoietic Characteristics", *Experimental Cell Research*, vol. 312, pp. 2454-2464, 2006.
Zhao, Y. et al., "A Unique Human Blood-Derived Cell Population Displays High Potential for Producing Insulin", *Biochemical and Biophysical Research Communications*, vol. 360, pp. 205-211, 2007.
Zhao, Y. et al., "Immune Regulation of T Lymphocyte by a Newly Characterized Human Umbilcal Cord Blood Stem Cell", *Immunology Letters*, vol. 108, pp. 78-87, 2007.
Rice et al., Adult stem cells—reprogramming neurological repair? Lancet. Jul. 10-16, 2004;364(9429):193-9.
Richards et al., Human feeders support prolonged undifferentiated growth of human inner cell masses and embryonic stem cells. Nat Biotechnol. Sep. 2002;20(9):933-6. Epub Aug. 5, 2002.
Sanberg et al., Umbilical cord blood-derived stem cells and brain repair. Ann N Y Acad Sci. May 2005;1049:67-83.
Sancho et al., CD69 is an immunoregulatory molecule induced following activation. Trends Immunol. Mar. 2005;26(3):136-40.
Segev et al., Differentiation of human embryonic stem cells into insulin-producing clusters. Stem Cells. 2004;22(3):265-74.
Shea et al., DNA delivery from polymer matrices for tissue engineering. Nat Biotechnol. Jun. 1999;17(6):551-4.
Shibasaki et al., Integration of ATP, cAMP, and Ca2+ signals in insulin granule exocytosis. Diabetes. Dec. 2004;53 Suppl 3:S59-62.
Silani et al., Stem-cell therapy for amyotrophic lateral sclerosis. Lancet. Jul. 10-16, 2004;364(9429):200-2.
Sutherland et al., Characterization and partial purification of human marrow cells capable of initiating long-term hematopoiesis in vitro. Blood. Oct. 1989;74(5):1563-70.
Taneera et al., Failure of transplanted bone marrow cells to adopt a pancreatic beta-cell fate. Diabetes. Feb. 2006;55(2):290-6.
Taylor et al., Curbing activation: proprotein convertases in homeostatsis and pathology. FASEB J. Jul. 2003;17(10):1215-27.
Thorens, B., GLUT2 in pancreatic and extra-pancreatic gluco-detection (review). Mol. Membr Biol. Oct.-Dec. 2001;18(4):265-73.
Tilden, J. Immunol, 1982, vol. 129, pp. 2469-2473.
Tsai, Hum. Reprod, 2004, vol. 19, pp. 1450-1456.
Underhill et al., The Toll-like receptor 2 is recruited to macrophage phagosomes and discriminates between pathogens. Nature. Oct. 21, 1999;401(6755):811-5.
Vats et al., Stems cells. Lancet. Aug. 13-19, 2005;366(9485):592-602.
Wagers et al., Plasticity of adult stem cells. Cell. Mar. 5, 2004;116(5):639-48.
Wilan et al., Chasing a cellular fountain of youth. Nat Biotechnol. Jul. 2005;23(7):807-15.
Yamada et al., Relationship between beta cell mass of NOD donors and diabetes development of NOD-scid recipients in adoptive transfer system. Ann N Y Acad Sci. Nov. 2003;1005:211-4.
Yanagi et al., Performance of a new hybrid artificial liver support system using hepatocytes entrapped within a hydrogel. ASAIO Trans. Jul.-Sep. 1989;35(3):570-2.
Yu et al., Mid-trimester fetal blood-derived adherent cells share characteristics similiar to mesenchymal stem cells but full-term umbilical cord blood does not. Br J Haematol. Mar. 2004;124(5):666-75.
Zalzaman et al., Reversal of hyperglycemia in mice by using human expandable insulin-producing cells differentiated from fetal liver progenitor cells. Proc Natl Acad Sci U S A. Jun. 10, 2003;100(12):7253-8. Epub May 19, 2003.
Zalzman et al., Differentiation of human liver-derived, insulin-producing cells toward the beta-cell phenotype. Diabetes. Sep. 2005;54(9):2568-75.
Ziche et al., Nitric oxide mediates angiogenesis in vivo and endothelial cell growth and migration in vitro promoted by substance P. J Clin Invest. Nov. 1994;94(5):2036-44.

* cited by examiner

SEQUENCE LISTING

```
<160> NUMBER OF SEQ ID NOS: 8

<210> SEQ ID NO 1
<211> LENGTH: 360
<212> TYPE: PRT
<213> ORGANISM: Homo sapiens
```

-continued

```
<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Pro Glu Pro Gly Trp Val Asp Pro
            20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
        50                  55                  60

Pro Pro Tyr Glu Phe Cys Gly Gly Met Ala Tyr Cys Gly Pro Gln Val
65              70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 2
<211> LENGTH: 1410
<212> TYPE: DNA
<213> ORGANISM: Homo sapiens
```

<400> SEQUENCE: 2

```
ccttcgcaag ccctcatttc accaggcccc cggcttgggg cgccttcctt ccccatggcg      60
ggacacctgg cttcggattt cgccttctcg cccctccag gtggtggagg tgatgggcca     120
gggggggccgg agccgggctg ggttgatcct cggacctggc taagcttcca aggccctcct    180
ggagggccag gaatcgggcc gggggttggg ccaggctctg aggtgtgggg gattccccca    240
gccccccgcc gtatgagttc tgtgggggga tggcgtactg tgggcccag gttggagtgg     300
ggctagtgcc ccaaggcggc ttggagacct ctcagcctga gggcgaagca ggagtcgggg    360
tggagagcaa ctccgatggg gcctcccgg agccctgcac cgtcaccct ggtgccgtga      420
agctggagaa ggagaagctg gagcaaaacc cggaggagtc ccaggacatc aaagctctgc    480
agaaagaact cgagcaattt gccaagctcc tgaagcagaa gaggatcacc ctgggatata    540
cacaggccga tgtgggctc accctggggg ttctatttgg gaaggtattc agccaaacga    600
ccatctgccg ctttgaggct ctgcagctta gcttcaagaa catgtgtaag ctgcggccct    660
tgctgcagaa gtgggtggag aagctgaca acaatgaaaa tcttcaggag atatgcaaag    720
cagaaaccct cgtgcaggcc cgaaagagaa agcgaaccag tatcgagaac cgagtgagag    780
gcaacctgga gaatttgttc ctgcagtgcc cgaaacccac actgcagcag atcagccaca    840
tcgcccagca gcttgggctc gagaaggatg tggtccgagt gtggttctgt aaccggcgcc    900
agaagggcaa gcgatcaagc agcgactatg cacaacgaga ggattttgag gctgctgggt    960
ctccttctc aggggacca gtgtcctttc tctggcccc agggcccat tttggtaccc       1020
caggctatgg gagccctcac ttcactgcac tgtactcctc ggtcccttc cctgaggggg     1080
aagcctttcc ccctgtctcc gtcaccactc tgggctctcc catgcattca aactgaggtg    1140
cctgcccttc taggaatggg ggacagggg agggaaggag ctagggaaag aaaacctgga    1200
gtttgtgcca gggttttgg gattaagttc ttcattcact aaggaaggaa ttgggaacac    1260
aaagggtggg ggcaggggag tttggggcaa ctggttggag ggaaggtgaa gttcaatgat    1320
gctcttgatt ttaatcccac atcatgtatc acttttttct taaataaga agcctgggac    1380
acagtagata gacacactta aaaaaaaaaa                                    1410
```

<210> SEQ ID NO 3
<211> LENGTH: 305
<212> TYPE: PRT
<213> ORGANISM: Homo sapiens

<400> SEQUENCE: 3

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110
```

```
Arg Phe Gln Arg Gln Lys Tyr Leu Ser Leu Gln Met Gln Glu Leu
            115                 120                 125

Ser Asn Ile Leu Asn Leu Ser Tyr Lys Gln Val Lys Thr Trp Phe Gln
        130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305

<210> SEQ ID NO 4
<211> LENGTH: 2098
<212> TYPE: DNA
<213> ORGANISM: Homo sapiens

<400> SEQUENCE: 4
attataaatc tagagactcc aggattttaa cgttctgctg gactgagctg gttgcctcat    60
gttattatgc aggcaactca ctttatccca atttcttgat acttttcctt ctggaggtcc   120
tatttctcta acatcttcca gaaaagtctt aaagctgcct taaccttttt tccagtccac   180
ctcttaaatt ttttcctcct cttcctctat actaacatga gtgtggatcc agcttgtccc   240
caaagcttgc cttgctttga agcatccgac tgtaaagaat cttcacctat gcctgtgatt   300
tgtgggcctg aagaaaacta tccatccttg caaatgtctt ctgctgagat gcctcacacg   360
gagactgtct ctcctcttcc ttcctccatg gatctgctta tcaggacag ccctgattct   420
tccaccagtc ccaaaggcaa caacccact tctgcagaga agagtgtcgc aaaaaaggaa   480
gacaaggtcc cggtcaagaa acagaagacc agaactgtgt ctcttccac ccagctgtgt   540
gtactcaatg atagatttca gagacagaaa tacctcagcc tccagcagat gcaagaactc   600
tccaacatcc tgaacctcag ctacaaacag gtgaagacct ggttccagaa ccagagaatg   660
aaatctaaga ggtggcagaa aaacaactgg ccgaagaata gcaatggtgt gacgcagaag   720
gcctcagcac ctacctaccc cagcctttac tcttcctacc accagggatg cctggtgaac   780
ccgactggga accttccaat gtggagcaac cagacctgga caattcaac ctggagcaac   840
cagacccaga acatccagtc ctggagcaac cactcctgga cactcagac tggtgcacc   900
caatcctgga caatcaggc ctggaacagt cccttctata actgtggaga ggaatctctg   960
```

-continued

```
cagtcctgca tgcagttcca gccaaattct cctgccagtg acttggaggc tgccttggaa    1020
gctgctgggg aaggccttaa tgtaatacag cagaccacta ggtatttttag tactccacaa   1080 accatggatt tattcctaaa ctactccatg aacatgcaac ctgaagacgt gtgaagatga    1140
gtgaaactga tattactcaa tttcagtctg acactggct gaatccttcc tctcccctcc    1200
tcccatccct cataggattt ttcttgtttg gaaaccacgt gttctggttt ccatgatgcc    1260
catccagtca atctcatgga gggtggagta tggttggagc ctaatcagcg aggtttcttt    1320
tttttttttt ttcctattgg atcttcctgg agaaaatact tttttttttt tttttttga    1380 aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccg ccacctcgcc cggctaatat tttgtatttt tagtagagac ggggtttcac    1560
tgtgttagcc aggatggtct cgatctcctg accttgtgat ccacccgcct cggcctcct    1620 aacagctggg atttacaggc gtgagccacc gcgccctgcc tagaaaagac attttaataa    1680
ccttggctgc cgtctctggc tatagataag tagatctaat actagtttgg atatctttag    1740
ggtttagaat ctaacctcaa gaataagaaa tacaagtaca aattggtgat gaagatgtat    1800
tcgtattgtt tgggattggg aggctttgct tatttttttaa aaactattga ggtaaagggt   1860
taagctgtaa catacttaat tgatttctta ccgttttgg ctctgttttg ctatatcccc     1920
taatttgttg gttgtgctaa tctttgtaga aagaggtctc gtatttgctg catcgtaatg    1980
acatgagtac tgctttagtt ggtttaagtt caaatgaatg aaacaactat ttttccttta    2040
gttgatttta ccctgatttc accgagtgtt tcaatgagta aatatacagc ttaaacat     2098
```

```
<210> SEQ ID NO 5
<211> LENGTH: 321
<212> TYPE: PRT
<213> ORGANISM: Homo sapiens

<400> SEQUENCE: 5

His Ser Ala Arg Met Tyr Asn Met Met Glu Thr Glu Leu Lys Pro Pro
1               5                   10                  15

Gly Pro Gln Gln Thr Ser Gly Gly Gly Gly Asn Ser Thr Ala Ala
            20                  25                  30

Ala Ala Gly Gly Asn Gln Lys Asn Ser Pro Asp Arg Val Lys Arg Pro
        35                  40                  45

Met Asn Ala Phe Met Val Trp Ser Arg Gly Gln Arg Arg Lys Met Ala
    50                  55                  60

Gln Glu Asn Pro Lys Met His Asn Ser Glu Ile Ser Lys Arg Leu Gly
65                  70                  75                  80

Ala Glu Trp Lys Leu Leu Ser Glu Thr Glu Lys Arg Pro Phe Ile Asp
                85                  90                  95

Glu Ala Lys Arg Leu Arg Ala Leu His Met Lys Glu His Pro Asp Tyr
            100                 105                 110

Lys Tyr Arg Pro Arg Arg Lys Thr Lys Thr Leu Met Lys Lys Asp Lys
        115                 120                 125

Tyr Thr Leu Pro Gly Gly Leu Leu Ala Pro Gly Gly Asn Ser Met Ala
    130                 135                 140

Ser Gly Val Gly Val Gly Ala Gly Leu Gly Ala Gly Val Asn Gln Arg
145                 150                 155                 160
```

Met Asp Ser Tyr Ala His Met Asn Gly Trp Ser Asn Gly Ser Tyr Ser
             165                 170                 175

Met Met Gln Asp Gln Leu Gly Tyr Pro Gln His Pro Gly Leu Asn Ala
        180                 185                 190

His Gly Ala Ala Gln Met Gln Pro Met His Arg Tyr Asp Val Ser Ala
            195                 200                 205

Leu Gln Tyr Asn Ser Met Thr Ser Ser Gln Thr Tyr Met Asn Gly Ser
        210                 215                 220

Pro Thr Tyr Ser Met Ser Tyr Ser Gln Gln Gly Thr Pro Gly Met Ala
225                 230                 235                 240

Leu Gly Ser Met Gly Ser Val Val Lys Ser Glu Ala Ser Ser Ser Pro
                245                 250                 255

Pro Val Val Thr Ser Ser Ser His Ser Arg Ala Pro Cys Gln Ala Gly
                260                 265                 270

Asp Leu Arg Asp Met Ile Ser Met Tyr Leu Pro Gly Ala Glu Val Pro
            275                 280                 285

Glu Pro Ala Ala Pro Ser Arg Leu His Met Ser Gln His Tyr Gln Ser
        290                 295                 300

Gly Pro Val Pro Gly Thr Ala Ile Asn Gly Thr Leu Pro Leu Ser His
305                 310                 315                 320

Met

<210> SEQ ID NO 6
<211> LENGTH: 1085
<212> TYPE: DNA
<213> ORGANISM: Homo sapiens

<400> SEQUENCE: 6
cacagcgccc gcatgtacaa catgatggag acggagctga agccgccggg cccgcagcaa      60
acttcggggg gcggcggcgg caactccacc gcggcggcgg ccggcggcaa ccagaaaaac     120
agcccggacc gcgtcaagcg gcccatgaat gccttcatgg tgtggtcccg cgggcagcgg     180
cgcaagatgg cccaggagaa ccccaagatg cacaactcgg agatcagcaa gcgcctgggc     240
gccgagtgga aacttttgtc ggagacggag aagcggccgt tcatcgacga ggctaagcgg     300
ctgcgagcgc tgcacatgaa ggagcacccg gattataaat accggccccg gcggaaaacc     360
aagacgctca tgaagaagga taagtacacg ctgcccggcg gctgctggcc cccggcggc     420 aatagcatgg cgagcggggt cggggtgggc gccggcctgg gcgcgggcgt gaaccagcgc     480
atggacagtt acgcgcacat gaacggctgg agcaacggca gctacagcat gatgcaggac     540
cagctgggct acccgcagca cccgggcctc aatgcgcacg gcgcagcgca gatgcagccc     600
atgcaccgct acgacgtgag cgccctgcag tacaactcca tgaccagctc gcagacctac     660
atgaacggct cgcccaccta cagcatgtcc tactcgcagc agggcacccc tggcatggct     720
cttggctcca tgggttcggt ggtcaagtcc gaggccagct ccagccccc tgtggttacc     780 tcttcctccc actccagggc gcctgccag gccgggacc tccgggacat gatcagcatg     840
tatctccccg gcgccgaggt gccggaaccc gccgccccca gcagacttca catgtcccag     900
cactaccaga gcggcccggt gcccggcacg gccattaacg gcacactgcc cctctcacac     960
atgtgagggc cggacagcga actggagggg ggagaaattt tcaaagaaaa acgagggaaa    1020
tgggaggggt gcaaagagg agagtaagaa acagcatgga gaaacccgg tacgctcaaa    1080 aaaaa                                                                1085

```
<210> SEQ ID NO 7
<211> LENGTH: 28
<212> TYPE: DNA
<213> ORGANISM: Artificial Sequence
<220> FEATURE:
<223> OTHER INFORMATION: primer sequence

<400> SEQUENCE: 7
aaagcggcag atggtcgttt ggctgaat                                              28

<210> SEQ ID NO 8
<211> LENGTH: 28
<212> TYPE: DNA
<213> ORGANISM: Artificial Sequence
<220> FEATURE:
<223> OTHER INFORMATION: primer sequence

<400> SEQUENCE: 8
tggcaggaga atttggctgg aactgcat                                              28
```

EMBRYONIC-LIKE STEM CELLS DERIVED FROM ADULT HUMAN PERIPHERAL BLOOD AND METHODS OF USE

CROSS-REFERENCE TO RELATED APPLICATION

This application claims the benefit of U.S. Provisional Patent Application Ser. No. 60/852,901, filed Oct. 18, 2006 and U.S. Provisional Patent Application Ser. No. 60/926,846, filed Apr. 30, 2007, the disclosures of which are incorporated by reference herein in their entirety.

BACKGROUND OF THE INVENTION

1. Field of the Invention

The present invention is related generally to compositions and methods of isolation and use of embryonic-like stem cells obtained from adult human peripheral blood. The present invention also relates to methods and compositions for the treatment of diabetes in subjects in need of such treatment.

2. Background of the Invention

The increasing prevalence of chronic human diseases, e.g. cardiovascular disease, diabetes, and neuronal degenerative diseases, presents a challenge to find more effective therapies. Stem cell-based therapy, including embryonic and adult stem cells, provides a rational treatment tool for regenerative medicine and has potential to revolutionize modern therapeutics [A. Vats, R. C. Bielby, N. S. Tolley, R. Nerem, J. M. Polak, Stem cells, Lancet 366 (2005) 592-602; M. A. Hussain, N. D. Theise, Stem-cell therapy for diabetes mellitus, Lancet 364 (2004) 203-205; C. M. Rice, N. J. Scolding, Adult stem cells—reprogramming neurological repair? Lancet 364 (2004) 193-199; L. M. Hoffman, M. K. Carpenter, Characterization and culture of human embryonic stem cells, Nat Biotechnol. 23 (2005) 699-708]. Because of their high potential for self renewal and pluripotent differentiation capability, embryonic stem (ES) cells have become a very active area of investigation [A. Vats, R. C. Bielby, N. S. Tolley, R. Nerem, J. M. Polak, Stem cells, Lancet 366 (2005) 592-602; L. M. Hoffman, M. K. Carpenter, Characterization and culture of human embryonic stem cells, Nat Biotechnol. 23 (2005) 699-708; K. H. Wilan, C. T. Scott, S. Herrera, Chasing a cellular fountain of youth, Nat Biotechnol. 23 (2005) 807-815]. Ethical concerns, however, have limited their availability and practical usefulness [C. Dennis, Check E, 'Ethical' routes to stem cells highlight political divide, Nature 437 (2005) 1076-1077; M. Evans, Ethical sourcing of human embryonic stem cells—rational solutions? Nat Rev Mol Cell Biol. 6 (2005) 663-667]. Leaving aside these ethical concerns, using in vitro fertilization (IVF) and altered nuclear transfer (ANT) to generate ES cells is made problematic by the complexity of required technologies [M. Evans, Ethical sourcing of human embryonic stem cells—rational solutions? Nat Rev Mol Cell Biol. 6 (2005) 663-667; D. A. Melton, G. Q. Daley, C. G. Jennings, Altered nuclear transfer in stem-cell research—a flawed proposal, N Engl J Med. 351 (2004) 2791-2792].

Recently, human umbilical cord blood has been used as a source of stem cells to repopulate the hematopoietic system and other organs [J. Bonde, D. A. Hess, J. A. Nolta, Recent advances in hematopoietic stem cell biology, Curr Opin Hematol. 11 (2004) 392-398; K. K. Ballen, New trends in umbilical cord blood transplantation, Blood 105 (2005) 3786-3792; D. A. Peterson, Umbilical cord blood cells and brain stroke injury: bringing in fresh blood to address an old problem, J Clin Invest. 114 (2004) 312-314; V. Silani, L. Cova, M. Corbo, A. Ciammola, E. Polli, Stem-cell therapy for amyotrophic lateral sclerosis, Lancet 364 (2004) 200-202]. Cord blood provides an abundant source for generation of stem cells, including mesenchymal stem cells [K. Bieback, S. Kern, H. Kluter, H. Eichler, Critical parameters for the isolation of mesenchymal stem cells from umbilical cord blood, Stem Cells 22 (2004) 625-634; E. J. Gang, S. H. Hong, J. A. Jeong, S. H. Hwang, S. W. Kim, I. H. Yang, C. Ahn, H. Han, H. Kim, In vitro mesengenic potential of human umbilical cord blood-derived mesenchymal stem cells, Biochem Biophys Res Commun. 321 (2004) 102-108; G. Kogler, S. Sensken, J. A. Airey, T. Trapp, M. Muschen, N. Feldhahn, S. Liedtke, R. V. Sorg, J. Fischer, C. Rosenbaum, S. Greschat, A. Knipper, J. Bender, O. Degistirici, J. Gao, A. I. Caplan, E. J. Colletti, G. Almeida-Porada, H. W. Muller, E. Zanjani, P. Wernet, A new human somatic stem cell from placental cord blood with intrinsic pluripotent differentiation potential, J Exp Med. 200 (2004) 123-135] and monocyte-derived stem cells [Y. Zhao, T. Mazzone, Human umbilical cord blood-derived f-macrophages retain pluripotentiality after thrombopoietin expansion, Exp Cell Res. 310 (2005) 311-318]. Stem cells expressing ES molecular markers have been reported from cord blood after removal of hematopoietic cells (including deletion of all leukocyte common antigen CD45 positive cells) [C. P. McGuckin, N. Forraz, M. O. Baradez, S. Navran, J. Zhao, R. Urban, R. Tilton, L. Denner, Production of stem cells with embryonic characteristics from human umbilical cord blood, Cell Prolif. 38 (2005) 245-55]. However, the scarcity of this previously-described cell population [C. P. McGuckin, N. Forraz, M. O. Baradez, S. Navran, J. Zhao, R. Urban, R. Tilton, L. Denner, Production of stem cells with embryonic characteristics from human umbilical cord blood, Cell Prolif. 38 (2005) 245-55] in cord blood significantly restricts its practical application.

Several other embryonic-like stem cells derived from adult sources rather than embryonic sources have also been disclosed. For example, U.S. Pat. No. 7,045,148, United States Patent Applications Serial Numbers. 2005/0148034, 2005/0118715, 2004/0028660, 2003/0235909, 2002/0160510, 2003/0180269 and International Patent Application Number WO 03/068937 disclose embryonic-like stem cells extracted from the placenta or from the umbilical cord blood. United States Patent Application Serial Number 2006/0078993 discloses embryonic-like stem cells derived from the amniotic membrane of umbilical cord. The stem cells disclosed in these patents or patent applications are of mesenchymal origin which do not express the CD45 marker (CD45−). In another example, United States Patent Application Serial Number 2006/0147426 discloses stem cells derived from human bone marrow. International Application PCT/US06/38524 by Zhao and Mazzone discloses an embryonic-like stem cell isolated from the umbilical cord blood that is suitable for stem cell therapies.

However, better methods of isolating autologous stem cells are needed to overcome the challenges faced by current stem cell research, such as ethical concerns and immune rejection. Accordingly, there is a need in the art for methods of isolation of stem cells with embryonic-stem cell characteristics from readily available sources in adults.

BRIEF SUMMARY OF THE INVENTION

In one aspect, the invention discloses a method of harvesting embryonic-like stem cells from peripheral blood comprising extracting peripheral blood comprising peripheral blood mononuclear cells (PBMCs); culturing the PBMCs in growth medium, such that the PBMCs revert to embryonic-like stem cells; and isolating the embryonic-like stem cells. In some embodiments, the growth medium comprises RPMI 1640 medium and fetal bovine serum. The cells do not require feeder cell layers to grow in vitro and does not form teratomas when grown in vivo. Red cells can be removed from peripheral blood to obtain PBMCs prior to culturing. Culturing can further include seeding the PBMC's on a surface with a net positive charge, such as polystyrene and glass. Isolating the embryonic-like stem cells includes removing the cells attached to the surface. For example, the cells can be incubated with a solution comprising lidocaine hydrochloride and/or ethylenediamine tetraacetic acid (EDTA). In some embodiments, a substantially homogeneous population of embryonic-like stem cell can be isolated.

In some embodiments, isolating the embryonic-like stem cells can further include selecting cell that have a positive marker for at least one of Octamer-binding transcription factor 4 (Oct-4), Nanog homeobox (Nanog), SRY (sex determining region Y)-box 2 (Sox-2), CD9, and CD45, a negative marker for at least one of CD3, CD20, CD11b/Mac-1, CD11c, and CD14; and a negative marker for CD 34.

In another aspect, the invention discloses a method of directing cell differentiation of embryonic-like stem cells by incubating the embryonic-like stem cells of the present invention with an inducer, wherein the inducer directs maturation of the embryonic-like stem cells into a defined population of cells. Non-limiting examples of inducers include Exendin-4, granulocyte monocyte colony stimulating factor (GM-CSF), granulocyte-macrophage colony-stimulating, nerve growth factor (NGF), 5-Aza-2'-deoxycytidine, retinoic acid (RA), dimethyl sulfoxide (DMSO), thrombopoietin, hepatocyte growth factor (HGF), vascular endothelial growth factor isoform165 (VEGF165), epidermal growth factor (EGF), erythropoietin (EPO), interleukin-2 (IL-2), IL-5, IL-7, IL-18, interferon-gamma, granulocyte-macrophage colony-stimulating factor (GM-CSF), macrophage colony-stimulating factor (M-CSF), phorbol 12-myristate 13-acetate (PMA), lipopolysaccharide (LPS), granulocyte colony-stimulating factor (G-CSF), all trans-retinoic acid (ATRA), vitaminD3, bone morphogenetic proteins (BMPs), brain derived neurotrophic factor (BDNF), glial derived neurotrophic factor (GDNF), growth factors, fibroblast growth factor (FGF), transforming growth factors (TGF), ciliary neurotrophic factor (CNTF), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, silencers, SHC (SRC-homology-2-domain-containing transforming protein), neuroproteins, proteoglycans, glycoproteins, neural adhesion molecules, and other cell-signalling molecules and mixtures, thereof. The defined population of cells can have properties of cells from the following non-limiting examples of cells: beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells. Differentiating can be carried out by transducing the cells with a vector that contains a nucleic acid encoding the inducer and expresses the inducer in the cells. The vector can be a plasmid, cosmid, bacteriophage, DNA virus, RNA virus, or retrovirus vector. For example, PB-SC can differentiate into hepatocytes when exposed to hepatocyte growth factor (HGF); into endothelial cells when exposed to vascular endothelial growth factor isoform165 (VEGF165); into epithelial cells when exposed to epidermal growth factor (EGF); into red blood cells when exposed to erythropoietin (EPO); into lymphocytes when exposed to interleukin-2 (IL-2), IL-5, IL-7, IL-18, interferon-gamma; into monocyte/macrophage when exposed to granulocyte-macrophage colony-stimulating factor (GM-CSF); into macrophage colony-stimulating factor (M-CSF) when exposed to phorbol, 12-myristate 13-acetate (PMA), lipopolysaccharide (LPS); into granulocyte when exposed to granulocyte colony-stimulating factor (G-CSF), all trans-retinoic acid (ATRA), vitaminD3; into osteoblast cells when exposed to bone morphogenetic proteins (BMPs).

In another aspect, the invention discloses an isolated embryonic-like stem cell harvested from human peripheral blood with a positive marker for at least one of Oct-4, Nanog, Sox-2, CD9, and CD45, a negative marker for at least one of CD3, CD20, CD11b/Mac-1, CD11c, and CD14; and a negative marker for CD 34. The isolated embryonic-like stem cell can further include at least one, or at least two, or preferably at least three of the following embryonic genes selected from the group consisting of Zinc finger protein 206 (ZNF206), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), and Zinc finger protein 589 (ZNF589).

In some embodiments, the isolated embryonic-like stem cell is capable of differentiating into insulin-producing cells. The insulin-producing cells can express at least one, or preferably at least two, or more preferably at least three insulin gene transcription factors. Non-limiting examples of insulin gene transcription factors include leucine zipper MafA, Pdx-1 (pancreatic duodenal homeobox factor 1), NeuroD1 (neurogenic differentiation 1), HNF6 (hepatocyte nuclear factor 6), Nkx6.1 (Nk homeobox gene), and Nkx2.2.

In another aspect, the invention discloses a method of suppressing lymphocytes in a subject in need thereof, comprising coculturing a first population of cells comprising embryonic-like stem cells with a second population of cells comprising lymphocytes, administering at least one of the treated first or second cell populations after coculturing to a subject. In some embodiments, the second cell population is administered. The lymphocytes can be allogeneic lymphocytes, or autologous lymphocytes from human peripheral blood. Culturing the lymphocytes with the embryonic-like stem cells modulates the lymphocytes. For example, the modulation can include decreasing intracellular IL-10 levels, increasing expression of CD69 on activated T lymphocytes, inhibiting proliferation of IL-2-stimulated lymphocytes and/or inhibiting proliferation of PHA-stimulated lymphocytes. Insulin production in the subject can be increased. The method can include up-regulating nitric oxide (NO) production. In some embodiments, the method can be used to treat, ameliorate the symptoms or delay onset of type I diabetes.

In yet another aspect, the invention discloses a method of treating diabetes in a mammalian subject in need thereof, comprising culturing embryonic-like stem cells from peripheral blood; and administering the cells to the subject in an amount effective to treat diabetes. The cells can be differentiated into insulin-producing cells. The administering step can be through any suitable method, for example, intravenous or intraarterial injection. The cells can be administered in an amount of from about $1 \times 10^4$-$1 \times 10^9$ cells per subject. The method can be used to treat or ameliorate the symptoms of insulin-dependent diabetes. In some embodiments, the cells are administered into the pancreas of the subject. In some embodiments, the cells are encapsulated in an insulin-permeable capsule.

In a preferred embodiment, the peripheral blood is obtained from the subject. Alternatively, the peripheral blood can be obtained from an allogenic or xenogenic source. The embryonic-like stem cells can be obtained through collecting peripheral blood comprising peripheral blood mononuclear cells (PBMCs); culturing the PBMCs ex-vivo, such that the PBMCs revert to embryonic-like stem cells; and isolating the embryonic-like stem cells. The PBMC's can be seeded on a hydrophobic surface with a net positive charge. Isolating the cells can include isolating the cells attached to the surface.

In yet another embodiments, the invention discloses a pharmaceutical composition useful for the treatment of diabetes comprising, peripheral-blood insulin-producing cells in a pharmaceutically acceptable carrier, wherein the peripheral-blood insulin-producing cells are derived from adult peripheral blood. The composition can be an injectable composition. In some embodiments, the cells are encapsulated in an insulin-permeable capsule. The peripheral-blood insulin-producing cells can express at least one insulin gene transcription factor, or preferably two or more insulin gene transcription factors.

DETAILED DESCRIPTION OF THE INVENTION

Figure 1:
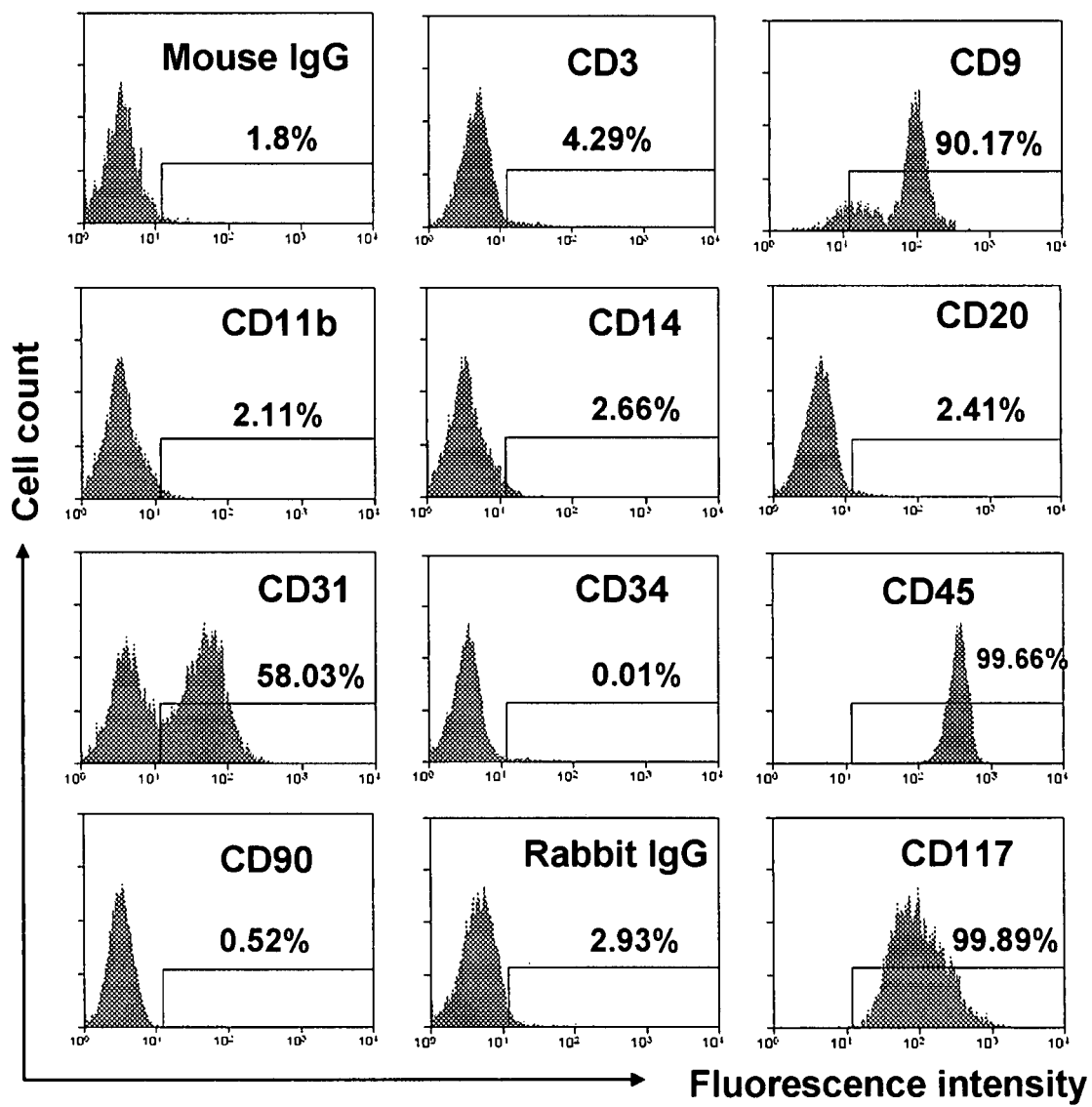
FIG. 1 depicts flow analysis data of hematopoietic cell markers on PB-SC.

The present invention discloses a novel type of stem cells isolated from adult human peripheral blood, designated herein as peripheral blood-stem cells (PB-SC). These novel stem cells are of blood (and not mesenchymal) origin as indicated by the high expression of the CD45 marker ($CD45^+$). These cells can be isolated and expanded using simple technology. PB-SC share properties with human ES cells and hematopoietic cells, including ability to proliferate and the ability to differentiate to other types of cells. Since these cells can be isolated from the peripheral blood of an individual, particularly an adult individual, they are suitable for autologous stem cell therapies. The present invention also discloses the use of PB-SC in differentiating to functional insulin-producing cells in vitro to control hyperglycemia in a diabetic mammalian subject.

The present invention discloses isolated embryonic-like stem cells from adult human peripheral blood, designated herein as PB-SC, which display embryonic stem cell characteristics; display hematopoietic cell characteristics, are phenotypically distinct from lymphocytes, macrophages and monocytes; and are phenotypically distinct from hematopoietic stem cells. These novel embryonic-like stem cells are capable of proliferation and are able to differentiate to other types of cells.

In a preferred embodiment, the embryonic stem characteristics include having phenotypes of positive for stem cell markers Oct-4 (SEQ ID. Nos: 1 and 2), Nanog (SEQ ID. NO. 3 and 4), and Sox-2 (SEQ ID. NO. 4 and 5), together with other embryonic stem (ES) cell-related genes, e.g., Zinc finger and SCAN domain containing 10 (ZNF206, also named ZSCAN10), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PT-PRZ1), Podocalyxin-like (PODXL), Polyhomeotic homolog 1 (PHC1), and Zinc finger protein 589 (ZNF589). The sequences for Oct-4, Nanog, and Sox-2 can be found under GenBank Accession Nos. NM_002701, Z11898 and Q01860; GenBank Accession Nos. NM_024865 and NP_079141; and GenBank Accession Nos. Z31560 and CAA83435, respectively.

In another embodiment, the hemotopoietic characteristics are characterized by being positive for the leukocyte common antigen CD45. In a further embodiment, the stem cells are phenotypically distinct from lymphocytes, dendritic cells, macrophages and monocytes by being negative for CD3, CD20 (B-lymphocyte cell-surface antigen B1, Accession No. M27394), CD11c (integrin, alpha X, Accession No. NM_000887), CD11b/Mac-1 (complement component 3 receptor 3 subunit, Accession No. NM_000632) and CD14 (Accession Nos. NM_001040021 and P08571) markers. In still another embodiment, the stem cells are phenotypically distinct from hematopoietic stem cells by being negative for CD34 marker (Hematopoietic progenitor cell antigen CD34, Accession No. P28906) (Craig et al. 1994, British Journal of Haematology, 88:24-30; Lansdorp, P. A I. and Dragowaka, W. (1992) J. Exp. Med. 175:1501-1509; Sutherland, H. J., et al. (1989), Blood 74.1563-1570.)).

In one embodiment, the embryonic-like stem cells of the present invention are capable of differentiating to other cells such as but are not limited to insulin-producing cells. PB-SC display the receptor of glucagon-like peptide 1 (GLP-1). Administration of exendin-4, a long-acting agonist of GLP-1, can improve their insulin production and cell differentiation. As shown in the Examples, the PB-SC give rise to functional insulin-producing cells when transplanted into the streptozotocin (STZ)-induced diabetic NOD-scid mice. In the present invention, we disclose that PB-SC exist in human blood (including adult peripheral blood) and have the capability to produce insulin. These cells are, therefore, also designated as peripheral blood derived insulin-producing cells (PB-IPC).

These PB-IPCs are capable of proliferation, producing insulin, and behave like islet β-islet cell progenitors. In some embodiments, the insulin producing cells can be characterized by positive expression of one or more insulin gene transcription factors. Examples of insulin gene transcription factor include but are not limited to leucine zipper MafA, Pdx-1 (pancreatic duodenal homeobox factor 1), NeuroD1 (neurogenic differentiation 1), HNF6 (hepatocyte nuclear factor 6, also known as Onecut1), Nkx6.1 (Nk homeobox gene), and Nkx2.2.

Since PB-SC can give rise to multiple cell types, such as but are not limited to, beta cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells in presence of different inducers, as demonstrated by displaying different lineage-specific markers and unique morphologies.

The present invention further discloses a composition for stem cell-based therapy comprising the embryonic-like stem cells of the present invention. In an embodiment, the embryonic-like stem cells of the present invention are used for treating hyperglycemia in a diabetic mammalian subject by administering the cells to the subject.

In yet another embodiment, the present invention discloses a method for isolating the embryonic-like stem cells of the present invention. The method comprises providing a sample of adult human peripheral blood; removing red cells from the sample to obtain mononuclear cells; culturing the mononuclear cells on a hydrophobic surface with a net positive charge and obtaining a cell population which is attached to the surface. The attached cell population can be detached from the surface by, for example, incubation with lidocaine hydrochloride. The lidocaine hydrochloride can be in the range of about 0.1% to about 5%. Optionally, the attached cells can be detached by further incubating the cells with EDTA solution or EDTA solution containing trypsin (trypsin/EDTA). The EDTA can be in the range from about 0.5 mM to about 2.5 mM, and the trypsin can be in the range from about 0.05% to about 0.25%. Furthermore, the cell culture does not require a cell feeder. These cells are suitable for stem cell-based therapies, particularly autologous stem cell therapies.

The terms used in this invention are, in general, expected to adhere to standard definitions generally accepted by those having ordinary skill in the art of molecular biology. A few exceptions, as listed below, have been further defined within the scope of the present invention.

As used herein, the terms "embryonic stem cell" refers to a stem cell that is derived from the inner cell mass of a blastocyst (e.g., a 4- to 7-day-old human embryo) and that is pluripotent. The terms "embryonic-like stem cell", "peripheral blood-stem cell (PB-SC)", and "peripheral blood derived insulin-producing cells (PB-IPC)" are used interchangeably herein to refer to a stem cell that is not derived from the inner cell mass of a blastocyst. An embryonic-like stem cell is pluripotent. The embryonic-like stem cells display at least a subset of characteristics of embryonic stem cells (ES) and hematopoietic cells.

As used herein, the term "pluripotential", "pluripotential for differentiation" or "pluripotent" refers that the cell is positive for one or more of the pluripotent markers such as but are not limited to Oct-4, Nanog, and Sox-2 and the cell has the potential to differentiate to at least a subset of the mammalian body's approximately 260 cell types upon appropriate stimulations such as by the appropriate growth factors.

As used herein, the term "totipotent cell" refers to a cell that is able to form a complete embryo (e.g., a blastocyst).

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. The "stem cell" used herein includes "progenitor cells" unless otherwise noted.

The term "subject" refers to any living organism in which an immune response is elicited. The term refers to a living animal or human in need of treatment for, or susceptible to, a condition involving an unwanted or undesirable microorganism, e.g., a particular treatment for having an unwanted pathogenic cell as defined below. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

The term "undifferentiated" as used herein refers to pluripotent embryonic stem cells which have not developed a characteristic of a more specialized cell. As will be recognized by one of skill in the art, the terms "undifferentiated" and "differentiated" are relative with respect to each other. A stem cell which is "differentiated" has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known markers of differentiation. A marker of differentiation indicating that cells are differentiated or undifferentiated includes a protein, carbohydrate, lipid, nucleic acid, functional characteristic and/or morphological characteristic which is specific to a differentiated cell.

As used herein, the term "substantially homogeneous" when applied to cells, refers to a population of cells, wherein at least about 70%, and preferably about 80%, more preferably 90% of the cells in the population are of the same cell type. Examples of cell types include, but are not limited to, embryonic-like stem cells, beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, retinal cells, and the like. In some embodiments, the term "substantially homogeneous" describes a population of cells wherein at least about 70%, and preferably about 80%, more preferably 90% of the cells in the population are undifferentiated. In a further embodiment a substantially homogeneous population of cells is one in which more than 95% of the cells are undifferentiated. In another embodiment, a substantially homogeneous population of cells is one in which more than 99% of the cells are undifferentiated. A population of cells can be assayed for one or more markers of differentiation to determine whether the population of cells is substantially homogeneous.

The production and/or maintenance of a substantially homogeneous population of embryonic-like stem cells and/or a differentiated cell type may be measured by assessing the proportion of cells for particular markers of undifferentiated cells and/or differentiated cells. For example, relative ratios of transcription products for markers of undifferentiated cells such as Oct4, neuroprogenitor markers such as nestin and Ngn-3, and markers of mature neuron markers such as β-tubulin and TPH2 is assessed by quantitative RT-PCR. Also, production and localization of markers of undifferentiated cells can be assessed by immunocytochemistry.

Markers of undifferentiated stem cells and differentiated cells are assayed by any of various methods such as antibody-based detection techniques using an antibody specific for a particular marker. Antibody-based techniques include immunofluorescence and immunoblotting. Further assays include assays for detection of mRNAs encoding a particular marker. Such assays include polymerase chain reaction, blot hybridization (also known as Northern blots) and in situ hybridization. Details of these and other such assays are described herein and in standard references including J. Sambrook and D. W. Russell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

As used herein, the term "culture medium" refers generally to any substance or preparation used for the cultivation of living cells. A "cell culture" refers to a growth of cells in vitro; although the cells proliferate they do not organize into tissue per se.

The term "administration" or "administering" is used throughout the specification to describe the process by which embryonic-like stem cells according to the present invention are delivered to a subject. The embryonic-like stem cells can be administered a number of ways including parenteral (such term referring to intravenous and intraarterial as well as other appropriate parenteral routes), intrathecal, intraventricular, intraparenchymal (including into the spinal cord, brainstem or motor cortex), intracisternal, intracranial, intrastriatal, and intranigral, among others which term allows the cells to migrate to the site where needed. The compositions according to the present invention can be used without treatment with an inducer ("untreated", i.e., without further treatment in order to promote differentiation of cells within the stem cell sample) or after treatment ("treated") with an inducer or other agent which causes the embryonic-like stem cells to differentiate into cells exhibiting a favorable phenotype. Administration will often depend upon the disease or condition treated and can preferably be via a parenteral route, for example, intravenously, by administration into the cerebral spinal fluid or by direct administration into the affected tissue in the brain or other body site. For example, in the case of diabetes, the preferred route of administration will into the pancreas. In the case of Alzheimer's disease, Huntington's disease and Parkinson's disease, the preferred route of administration will be a transplant directly into the striatum (caudate cutamen) or directly into the substantia nigra (Parkinson's disease). In the case of amyotrophic lateral sclerosis (Lou Gehrig's disease) and multiple sclerosis, the preferred administration is through the cerebrospinal fluid. In the case of lysosomal storage disease, the preferred route of administration is via an intravenous route or through the cerebrospinal fluid. In the case of stroke, the preferred route of administration will depend upon where the stroke is, but will often be directly into the affected tissue (which may be readily determined using MRI or other imaging techniques). In the case of heart disease, the method of administration can be by direct infusion into the affected area, or it can be by the intravenous route to allow transmigration through the circulatory system and "homing" to the affected site.

The terms "grafting" and "transplanting" and "graft" and "transplantation" are used throughout the specification synonymously to describe the process by which embryonic-like stem cells or other cells according to the present invention are delivered to the site where the cells are intended to exhibit a favorable effect, such as repairing damage to a patient's central nervous system, treating autoimmune diseases, treating diabetes, treating neurodegenerative diseases, or treating the effects of nerve, muscle and/or other damage caused by birth defects, stroke, cardiovascular disease, a heart attack or physical injury or trauma or genetic damage or environmental insult to the body, caused by, for example, disease, an accident or other activity. The embryonic-like stem cells or other cells for use in the present invention can also be delivered in a remote area of the body by any mode of administration as described above, relying on cellular migration to the appropriate area in the body to effect transplantation.

The term "essentially" is used to describe a population of cells or a method which is at least 90% effective, more preferably at least about 95% effective and even more preferably at least 98% effective. Thus, a method which "essentially" eliminates a given cell population, eliminates at least about 90% of the targeted cell population, most preferably at least about 98% of the cell population. Embryonic-like stem cells according to the present invention, in certain preferred embodiments, are essentially free of hematopoietic cells (i.e., negative for hematopoietic stem cell marker CD34), essentially free of lymphocyte (i.e., negative for lymphocyte markers CD3, CD20, and CD90), essentially free of monocyte/macrophage antigens CD11b/Mac-1 and CD14, essentially free of dendritic cell antigen CD11c, and essentially free of mesenchymal (CD45$^-$) cells.

The term "non-tumorigenic" refers to the fact that the cells do not give rise to a neoplasm or tumor. The embryonic-like stem cells for use in the present invention are generally free from neoplasia and cancer.

The term "inducer," as used herein, describes agents which may be added to cell culture (which term includes any cell culture medium which may be used to grow differentiated cells according to the present invention) containing pluripotent stem which will induce the cells to a desired cellular phenotype. Non-limiting examples of induces for use in the present invention include, for example, Exendin-4, granulocyte monocyte colony stimulating factor (GM-CSF), granulocyte-macrophage colony-stimulating, nerve growth factor (NGF), 5-Aza-2'-deoxycytidine, retinoic acid (RA), dimethyl sulfoxide (DMSO), thrombopoietin, hepatocyte growth factor (HGF), vascular endothelial growth factor isoform165 (VEGF165), epidermal growth factor (EGF), erythropoietin (EPO), interleukin-2 (IL-2), IL-5, IL-7, IL-18, interferon-gamma, granulocyte-macrophage colony-stimulating factor (GM-CSF), macrophage colony-stimulating factor (M-CSF), phorbol 12-myristate 13-acetate (PMA), lipopolysaccharide (LPS), granulocyte colony-stimulating factor (G-CSF), all trans-retinoic acid (ATRA), vitaminD3, bone morphogenetic proteins (BMPs), brain derived neurotrophic factor (BDNF), glial derived neurotrophic factor (GDNF), growth factors, fibroblast growth factor (FGF), transforming growth factors (TGF), ciliary neurotrophic factor (CNTF), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, silencers, SHC(SRC-homology-2-domain-containing transforming protein), neuroproteins, proteoglycans, glycoproteins, neural adhesion molecules, and other cell-signalling molecules and mixtures, thereof.

Isolation of Peripheral Blood—Stem Cells from Adult Human Peripheral Blood

The present invention discloses a population of novel embryonic-like stem cells isolated from adult human peripheral blood. They are designated herein as peripheral blood-stem cells (PB-SC).

According to the methods of the invention, PB-SC represent the attached population of cells obtained from culturing the mononuclear cells of the adult human peripheral blood after the removal of the red blood cells. These cells are generated using a very basic cell culture medium with a low percentage of serum (e.g., 7% fetal bovine serum), and without cell feeders. This is in contrast to ES cells generated using cell feeders. The requirement of cell feeders for such cells raises potential contamination problems [M. Richards, C. Y. Fong, W. K. Chan, P. C. Wong, A. Bongso, Human feeders support prolonged undifferentiated growth of human inner cell masses and embryonic stem cells, Nat Biotechnol. 20 (2002) 933-936]. An exemplified method of obtaining the PB-SC is shown in Example 1 below. The attached cell population can be detached from the positively charged surface by, for example, incubation in lidocaine hydrochloride solution wherein the lidocaine hydrochloride is from about 0.1% to about 5%. Optionally, the attached cells can be detached by further incubating the cells with EDTA solution or EDTA solution containing trypsin (trypsin/EDTA) wherein the EDTA is from about 0.5 mM to about 2.5 mM, and the trypsin is from about 0.05% to about 0.25%.

What is meant by "isolated" in the present invention is that the PB-SC are separated from other cells, such as the red blood cells and other unattached mononuclear cells, found in the umbilical cord blood through one or more isolation methods such as, but are not limited to, mechanical separation or selective culturing. The "isolated" PB-SC population does not have to be pure. Other cell types may be present. The other cell types present may be totally different from PB-SC, or they may be transformed from PB-SC during the cell culture and subsequent passage of the cells. In a preferred embodiment, the isolated population is made up of greater than 50% PB-SC. In yet another preferred embodiment, the isolated population is made up of greater than 75% PB-SC. In a further preferred embodiment, the isolated population is made up of greater than 90% PB-SC.

PB-SC Displaying Embryonic Stem (ES) Cell Characteristics

PB-SC in the present invention displays embryonic stem (ES) cell characteristics. What is meant by "embryonic stem cell characteristics" in the present invention is that the stem cells express critical transcription factors, Oct-4, Nanog and Sox2, which are related to the self-renewal and pluripotentiality of ES cells [S. H. Orkin, Chipping away at the Embryonic Stem Cell Network, Cell 122 (2005) 828-830]. In a preferred embodiment, markers characteristic of embryonic stem cell also include other markers such as but are not limited to the stage-specific embryonic antigen SSEA-3 and SSEA-4 [I. Klimanskaya, Y. Chung, L. Meisner, J. Johnson, M. D. West, R. Lanza, Human embryonic stem cells derived without feeder cells, Lancet 365 (2005) 1636-1641]. In yet another preferred embodiment, the "embryonic stem cell characteristics" may further include the weak expression of tumor rejection antigens such as but are not limited to TRA-1-60 and TRA-1-81. In a further embodiment, the "embryonic stem cell characteristics" may further include no expression of SSEA-1. In yet another preferred embodiment, the "embryonic stem cell characteristics" may further include expressions of other embryonic stem (ES) cell-related genes (FIG. 8A), e.g., Zinc finger and SCAN domain containing 10 (ZNF206, also named ZSCAN10), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), Polyhomeotic homolog 1 (PHC1), and Zinc finger protein 589 (ZNF589).

PB-SC Displaying Hematopoietic Cell Characteristics

PB-SC of the present invention displays hematopoeitic characteristics, which herein is defined as being positive for the leukocyte common antigen CD45 (CD45 positive, or CD45+). Other markers that also indicate displaying of hematopoietic cell characteristics may include markers such as, but are not limited to, tetraspanin CD9 and stem cell factor receptor CD117.

CB-SC Phenotyptically Different from Lymphocytes, Macrophages and Monocytes

Attached cells in blood are usually regarded as "macrophages". However, PB-SC do not express human monocyte/macrophage specific antigens CD14 and CD11b/Mac-1 (FIG. 1). These results indicate that CB-SC are phenotypically distinct from lymphocytes, macrophages and monocytes, and CB-SC are not monocyte-derived.

CB-SC have the Capability for Proliferation

One of the key characteristics for a stem cell to be suitable for stem cell-based therapy is its capability for proliferation. As used herein, the term "capability for proliferation" refers that the cell expresses one or more self-renewal markers such as but are not limited to Nanog and the cell can proliferate. Preferably, the cell can proliferate indefinitely. What is meant by "proliferate" as used in the present disclosure is that the cell can grow and multiply in numbers when the cell is cultured. The terms "proliferate" and "expand" are used interchangeably herein.

Figure 2:
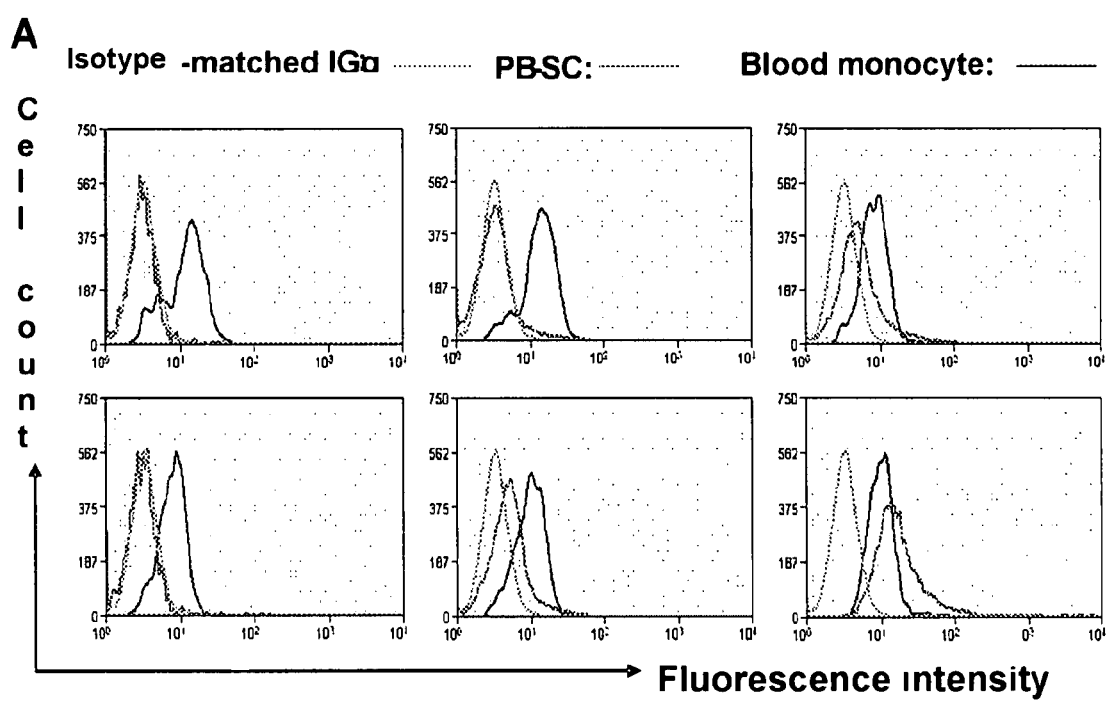
FIG. 2A depicts flow analysis data on immune response-associated phenotypes showing that PB-SC are different from monocytes/macrophages.
FIG. 2B depicts bar graphs comparing cell quantification of cell cultures of monocytes and macrophages, after removal of attached monocytes and macrophages (Mono/Macro), and whole PBMC.
Figure 2B:
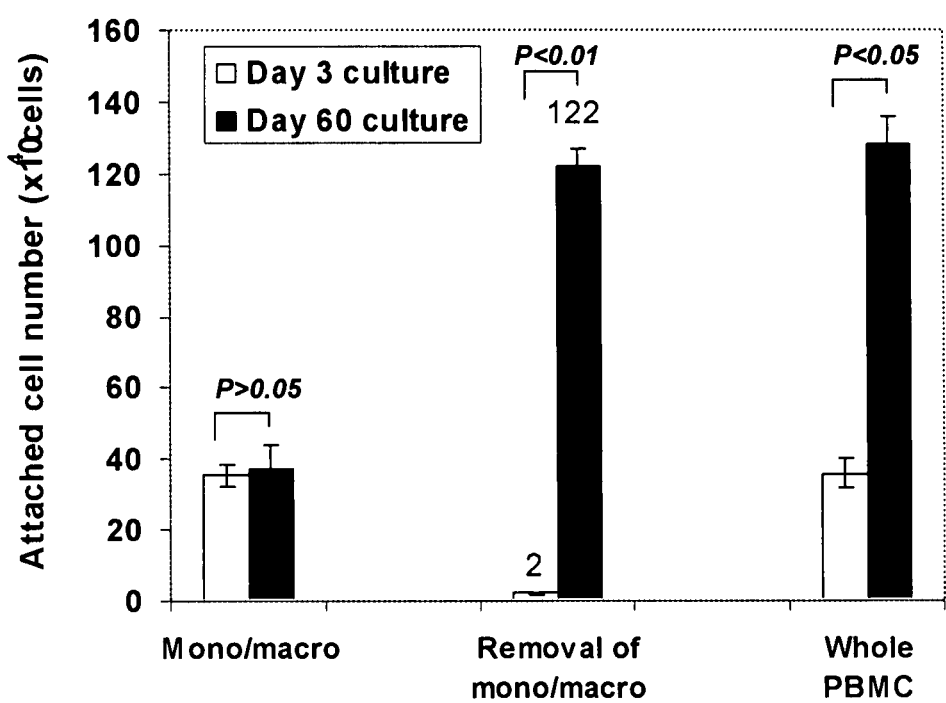

After culture for 2 months, PB-SC significantly increased in cell number (FIG. 2B). Based on the data, we calculated the doubling time of PB-SC was about 5.6 days.

Use of PB-SC for Treating Hyperglycemia in Diabetic Subjects

The present invention further provides a method for treating hyperglycemia in a diabetic mammalian subject by administering PB-SC to the subject. The administered PB-SC migrate to the pancreas of the subject and differentiate to functional insulin-producing cells in vivo, which in turn produce insulin in response to the high glucose level to control hyperglycemia in the subject. In an embodiment, the PB-SC is autologous in which they are prepared from the same individual in which the treatment is intended.

Diabetes is a dominant health problem. Deficit of insulin-producing cells is the crucial issue for both type 1 and type 2 diabetes. Stem cell-derived insulin-producing cells may provide a rational tool for treatment [M. A. Hussain, N. D. Theise, *Lancet* 364, 203 (2004); A. Vats, R. C. Bielby, N. S. Tolley, R. Nerem, J. M. Polak, *Lancet* 366, 592 (2005)]. The key to success for this therapy is the necessity to identify cells that are easy to access, select, culture, expand, and differentiate, without any ethical issues and immune rejection. Both embryonic and adult stem cells can serve as potential sources for clinical therapeutics [M. A. Hussain, N. D. Theise, *Lancet* 364, 203 (2004); A. Vats, R. C. Bielby, N. S. Tolley, R. Nerem, J. M. Polak, *Lancet* 366, 592 (2005); A. J. Wagers, I. L. Weissman, *Cell* 116, 639 (2004)]. However, immune system will recognize and attack foreign cells due to the immune surveillance of human body, even the application of allogeneic embryonic stem cells [J. A. Bradley, E. M. Bolton, R. A. Pedersen, *Nat Rev Immunol.* 2, 859 (2002); M. Drukker, et al. *Proc. Natl Acad. Sci.* 99, 9864 (2002)] Therefore, application of autologous stem cells is a potentially attractive strategy. Increasing evidence shows that human bone marrow and peripheral blood have provided valuable sources for generation of autologous stem cells [J. E. Grove, E. Bruscia, D. S Krause, *Stem Cells* 22, 487 (2004)], including CD34$^+$ hematopoietic stem cells, mesenchymal stem cells, and monocyte-derived stem cells [Y. Zhao, D. Glesne, E. Huberman, *Proc Natl Acad Sci USA* 100, 2426 (2003); M. Kuwana, et al, *J. Leukoc. Biol.* 74, 833 (2003)]. Nonetheless, it is unclear whether these adult stem cells can differentiate into insulin-producing cells [A. Ianus, G. G. Holz, N. D. Theise, M. A. Hussain, *J Clin Invest.* 111, 843 (2003); A. Ianus, G. G. Holz, N. D. Theise, M. A. Hussain, *J Clin Invest.* 111, 843 (2003); A. Lechner, et al, *Diabetes* 53, 616 (2004); J. Taneera, et al, *Diabetes* 55, 290 (2006)]. Recently, umbilical cord blood provides an alternative source to generate stem cells [K. K. Ballen, *Blood* 105, 3786 (2005)].

As shown in Example 2, below, PB-SC administered to streptozotocin (STZ)-induced diabetic mice differentiated to insulin-producing cells in vivo. Western blot demonstrated that PB-SC strongly expressed NeuroD, PDX-1 (a well-known transcription factor essential for beta cell development), and NKX6.1 (that commits pancreatic progenitors to β cells). PB-SC also expressed prohormone convertase PC1 and PC2, which are usually presented in islet β cells and other cellular tissues associated with peptide synthesis [X. Zhu, et al, *Proc Natl Acad Sci USA*. 99, 10299 (2002)]. Immunostaining showed PB-SC were positive for insulin and C-peptide (a by-product of insulin production, images not shown). In addition, PB-SC also displayed other β-cell markers. 70-80% of PB-SC displayed Glut-2, GCKR, and Sur1; >95% of cells showed alpha 1C; no expression of glucagon. PB-SC, when transplanted to STZ-induced diabetic mice, significantly reduced blood glucose levels. Altogether, these results strongly demonstrated that PB-SC can produce insulin and PB-SC can be potentially used for autologous transplantation to treat diabetes in adult human.

PB-SC Can Differentiate into Different Cell Types

As demonstrated below, PB-SC can differentiate into different cell types with and without the use of an inducer. In another aspect, the invention discloses a method of directing cell differentiation of embryonic-like stem cells by incubating the embryonic-like stem cells of the present invention with an inducer, wherein the inducer directs maturation of the embryonic-like stem cells into a defined population of cells. Non-limiting examples of inducers include Exendin-4, granulocyte monocyte colony stimulating factor (GM-CSF), granulocyte-macrophage colony-stimulating, nerve growth factor (NGF), 5-Aza-2'-deoxycytidine, retinoic acid (RA), dimethyl sulfoxide (DMSO), thrombopoietin, hepatocyte growth factor (HGF), vascular endothelial growth factor isoform165 (VEGF165), epidermal growth factor (EGF), erythropoietin (EPO), interleukin-2 (IL-2), IL-5, IL-7, IL-18, interferon-gamma, granulocyte-macrophage colony-stimulating factor (GM-CSF), macrophage colony-stimulating factor (M-CSF), phorbol 12-myristate 13-acetate (PMA), lipopolysaccharide (LPS), granulocyte colony-stimulating factor (G-CSF), all trans-retinoic acid (ATRA), vitaminD3, bone morphogenetic proteins (BMPs), brain derived neurotrophic factor (BDNF), glial derived neurotrophic factor (GDNF), growth factors, fibroblast growth factor (FGF), transforming growth factors (TGF), ciliary neurotrophic factor (CNTF), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, silencers, SHC (SRC-homology-2-domain-containing transforming protein), neuroproteins, proteoglycans, glycoproteins, neural adhesion molecules, and other cell-signalling molecules and mixtures, thereof. The defined population of cells can have properties of cells from the following non-limiting examples of cells: beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells. Differentiating can be carried out by transducing the cells with a vector that contains a nucleic acid encoding the inducer and expresses the inducer in the cells. The vector can be a plasmid, cosmid, bacteriophage, DNA virus, RNA virus, or retrovirus vector.

In one preferred embodiment the differentiating step is carried out by transducing (sometimes also referred to as "engineering" or "transforming") the cells with a vector, or introducing into the cells a vector, that contains a nucleic acid encoding an inducer and expresses the inducer in the cells, or by activating the expression of an endogeneous nucleic acid encoding an inducer in the cells (e.g., engineering the cells to activate transcription of an endogeneous such as granulocyte monocyte colony stimulating factor (GM-CSF), granulocyte-macrophage colony-stimulating, nerve growth factor (NGF), retinoic acid (RA), thrombopoietin, hepatocyte growth factor (HGF), epidermal growth factor (EGF), erythropoietin (EPO), interleukin-2 (IL-2), IL-5, IL-7, IL-18, interferon-gamma, granulocyte-macrophage colony-stimulating factor, etc., such as by inserting a heterologous promoter in operative associated with an endogeneous differentiation factor, in accordance with known techniques. See, e.g., U.S. Pat. No. 5,618,698). Such exogenous nucleic acids may be of any suitable source, typically mammalian, including but not limited to rodent (mouse, hamster, rat), dog, cat, primate (human, monkey), etc.

For recombinant techniques any suitable vector may be used, including plasmids, cosmids, bacteriophages, DNA viruses, RNA viruses and retroviruses, all of which are known for the expression of a heterologous nucleic acid in stem cells, progenitor cells, etc., in substantially the same manner as known. See, e.g., U.S. Pat. Nos. 6,392,118; 6,309,883; 6,258, 354; and 4,959,313. Such adenovirus vectors are also known and can be utilized in accordance with known techniques. See, e.g., U.S. Pat. Nos. 6,544,780; 6,503,498; 5,981,225;

and 5,670,488; Since transient expression is useful in carrying out the present invention, the vector may be simply "naked", or linear, DNA. The vector should include a suitable promoter (such as an SV40 promoter, retrovirus LTR-promoter, or cytomegalovirus (CMV) promoter), operatively associated with the nucleic acid to constituitively express, or inducibly express, the differentiation factor in the cells. Expression may be stable expression or transient expression depending upon the specific system chosen, with transient expression currently preferred.

The cells can be protected from immune rejection by modifying cell expression of selected proteins in accordance with known techniques. See, e.g., US Patent Application 2002/0182728. For example, the cultured transdifferentiated cells can be transformed to express a protein or peptide which will inhibit or prevent the destructive immune process. Other useful proteins or peptides may be expressed. In addition, expression of autoantigens specific to the IDD process, such as GAD, 64 kD islet cell surface antigens, to the extent they may be expressed by the transdifferentiated cells, or any other markers identified on the cells, can be eliminated by standard gene knock-out or selection procedures to produce cells which are not or are less susceptible to autoimmune attack. Methods for producing such mutant or knock out cells are well known in the art and include, for example, homologous recombination methods disclosed in U.S. Pat. Nos. 5,286,632; 5,320,962; 5,342,761; and in WO 90/11354; WO 92/03917; WO 93/04169; WO 95/17911, all of which are herein incorporated in their entirety by reference. In addition, a universal donor cell is produced by preparing transdifferentiated cells modified so as not to express human leukocyte antigen (HLA) markers.

If desired the cells can be frozen or cryopreserved prior to use, and then thawed to a viable form. Methods of freezing or cryopreserving cells (for subsequent return to viable form) are well known in the art. For example, cryopreservation of cells can involve freezing the cells in a mixture of a growth medium and another liquid that prevents water from forming ice crystals, and then storing the cells at liquid nitrogen temperatures (e.g., from about −80 to about −196 C.). See, e.g., U.S. Pat. No. 6,783,964 to Opara.

Formulations and Administration

PBSCs or their differentiated progeny can be administered to a subject by a several methods available to the art, including but not limited to localized injection, catheter administration, systemic injection, intraperitoneal injection, parenteral administration, intracranial injection, intra-arterial injection, intravenous injection, intraplacental injection, intrauterine injection, intrathecal administration, intraventricular administration, intracisternal administration, intrastriatal administration, intranigral administration, intramuscular injection, surgical injection into a tissue of interest or via direct application to tissue surfaces (e.g., during surgery or on a wound).

A method to potentially increase cell survival is to incorporate PBSCs or other cells of interest into a biopolymer or synthetic polymer. Depending on the patient's condition, the site of injection might prove inhospitable for cell seeding and growth because of scarring or other impediments. Examples of biopolymer include, but are not limited to cells mixed with fibronectin, fibrin, fibrinogen, thrombin, collagen, and proteoglycans. This could be constructed with or without included cytokines, differentiation factors, angiogenesis factors and/or anti-apoptosis factors. Additionally, these could be in suspension. Another alternative is a three-dimension gel with cells entrapped within the interstices of the cell biopolymer admixture. Again cytokines, differentiation factors, angiogenesis factors and/or anti-apoptosis factors could be included within the gel. These could be deployed by injection via various routes described herein, via catheters or other surgical procedures.

The quantity of cells to be administered will vary for the subject being treated. In a preferred embodiment, between about $10^3$ to about $10^9$, more preferably about $10^4$ to about $10^8$, more preferably about $10^5$ to about $10^7$ PBSCs can be administered to a human subject. The precise determination of what would be considered an effective dose may be based on factors individual to each patient, including their size, age, disease or injury, size of damage caused by the disease or injury and amount of time since the damage occurred.

When administering a therapeutic composition of the present invention, it will generally be formulated in a unit dosage injectable form (solution, suspension, emulsion). The doses may be single doses or multiple doses over a period of several days. The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, PBSCs can be administered initially, and thereafter maintained by further administration of PBSCs. For instance, PBSCs can be administered by one method of injection, and thereafter further administered by a different or the same method.

Examples of compositions comprising PBSCs or differentiated progeny thereof, include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as Remington, The Science And Practice of Pharmacy (9.sup.th Ed. 1995), incorporated herein by reference, may be consulted to prepare suitable preparations, without undue experimentation. In the manufacture of a pharmaceutical formulation according to the invention, the cells are typically admixed with an acceptable carrier. The carrier must, of course, be acceptable in the sense of being compatible with any other ingredients in the formulation and must not be deleterious to the patient. The carrier may be a solid or a liquid, or both (e.g., hydrogels), and may be formulated with the cells as a unit-dose formulation. In one embodiment the cells are provided as a suspension in the carrier to reduce clumping of the cells.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, PVA, ethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, they will not affect the viability or efficacy of the cells as described in the present invention.

Compositions can be administered in dosages and by techniques available to those skilled in the medical and veterinary arts taking into consideration such factors as the age, sex, weight, and condition of the particular subject, and the composition form used for administration (e.g., solid vs. liquid).

Matrices are also used to deliver cells of the present invention to specific anatomic sites, where particular growth factors incorporated into the matrix, or encoded on plasmids incorporated into the matrix for uptake by the cells, can be used to direct the growth of the initial cell population. DNA can be incorporated within pores of the matrix, for example, during the foaming process used in the formation of certain polymer matrices. As the polymer used in the foaming process expands, it entraps the DNA within the pores, allowing controlled and sustained release of plasmid DNA. Such a method of matrix preparation is described by Shea, et al. (Nature Biotechnology (1999) 17: 551-554).

Plasmid DNA encoding cytokines, growth factors, or hormones can be trapped within a polymer gene-activated matrix carrier, as described by Bonadio, J., et al. (Nature Medicine (1999) 5: 753-759). The biodegradable polymer is then implanted near the brain or other neural tissue, where PBSCs are implanted and take up the DNA, which causes the PBSCs to produce a high local concentration of the cytokine, growth factor, or hormone, accelerating healing of the damaged tissue.

In some embodiments, the PBSCs are encapsulated. One goal in encapsulation in cell therapy is to protect allogeneic and xenogeneic cell transplants from destruction by the host immune response, thereby eliminating or reducing the need for immuno-suppressive drug therapy. Techniques for microencapsulation of cells are available to the art (see, for example, Chang, P., et al., Trends in Biotech. 1999; 17:78-83; Matthew, H. W., et al., ASAIO Trans. 1991; 37(3):M328-30; Yanagi, K., et al., ASAIO Trans. 1989; 35(3):570-2; Cai Z. H., et al., Artif Organs. 1988; 12(5):388-93; Chang, T. M., Artif Organs. 1992; 16(1):71-4). Materials for microencapsulation of cells include, for example, polymer capsules, dendrimer, liposome, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275, for example, describes improved devices and methods for long-term, stable expression of a biologically active molecule using a biocompatible capsule containing genetically engineered cells.

For the purposes described herein, either autologous, allogeneic or xenogenic PBSCs of the present invention can be administered to a subject, either in differentiated or undifferentiated form, genetically altered or unaltered, by direct injection to a desired site, systemically, on or around the surface of an acceptable matrix, or in combination with a pharmaceutically acceptable carrier.

Following transplantation, the growth and/or differentiation of the administered PBSCs or their differentiated progeny, and the therapeutic effect of the PBSCs or progeny may be monitored. For example, the functionality of PBSCs administered to treat damaged neuronal tissue may be monitored by analyzing behavioral studies before an after administration of the PBSCs, or the functionality of PBSCs administered to treat diabetes by monitoring blood glucose and/or insulin levels.

Following administration, the immunological tolerance of the subject to the PBSCs or progeny derived therefrom may be tested by various methods known in the art to assess the subject's immunological tolerance to PBSCs or progeny derived therefrom. In cases where subject's tolerance of PBSCs or progeny derived therefrom is suboptimal (e.g., the subject's immune system is rejecting the exogenous PBSCs), therapeutic adjunct immunosuppressive treatment, which is available to the art, of the subject may be performed.

EXAMPLES

This invention is further illustrated by the following examples which should not be construed as limiting. The following experiments were performed to demonstrate various aspects of the invention.

Statistical analyses of data in the following examples were performed by the paired Student's t-test to determine statistical significance. Values are given as mean±SD (standard deviation).

Mouse anti-human monoclonal antibodies to CD3, CD9, CD11b/Mac-1 (Clone ICRF44), CD14, FITC-conjugated CD14 (clone M5E2), CD20, CD31, CD34 (clone 563), R-PE-conjugated mouse anti-human CD34 monoclonal antibody (clone 563), CD45 (clone HI30), FITC-conjugated CD45, human leukocyte antigen (HLA)-DR, HLA-DQ, HLAABC, isotype-matched antibody IgG1κ, and FITC-conjugated IgG were purchased from BD Pharmingen (San Diego, Calif.). Mouse monoclonal antibodies to human CD40, CD80 (B7-1), CD86 (B7-2), CXCR4, and rabbit anti-mouse CXCL12 alpha subunit (SDF-1α) were from eBioscience (San Diego, Calif.). Mouse anti-human Thy-1 (CD90), embryonic transcription factor Oct-4 monoclonal antibodies, rabbit anti-human embryonic transcription factor Nanog and alpha 1C (Cav1.2) polyclonal antibodies were from Chemicon International Inc. (Temecula, Calif.). Rabbit anti-human polyclonal antibody CD117 was from NeoMarkers. Rabbit anti-human polyclonal antibodies: PDX-1, NeuroD, NKX6.1, Glut-2, Sur1, glucokinase regulator protein (GCKR) and normal rabbit IgG were from Santa Cruz Biotechnology (Santa Cruz, Calif.); PC-1 (also named PC1/3) and PC-2 were from Abcam (Cambridge, Mass.). Recombinant human macrophage colony-stimulating factor (M-CSF), mouse anti-human insulin, and anti-glucagon monoclonal antibodies were purchased from Sigma (St. Louis, Mo.). FITC- or Rhodamine (TRITC)-labeled AffiniPure Donkey anti-mouse IgG antibody was obtained from Jackson ImmunoResearch Laboratories (West Grove, Pa.). Alexa Fluor 568-labeled goat anti-rabbit IgG (H+L) highly cross-adsorbed second antibody and Zymosan A BioParticles were from Molecular Probes (Eugene, Oreg.).

Example 1

Isolation of Embryronic-like Stem Cells from Adult Human Peripheral Blood

Cell Culture

Human buffy coats (50-60 ml/unit) were obtained from 10 healthy donors (6 male and 4 female), aged 20-62 years (averaged 45±13) (Life-Source Blood Services, Glenview, Ill.). Mononuclear cells were isolated using Ficoll-Hypaque ($\gamma$=1.077, Sigma), followed by removing red blood cells using Red Blood Cell Lysis buffer (eBioscience, San Diego, Calif.). PB-SC culture was performed as previously described [Y. Zhao, H. Wang, T. Mazzone. Exp Cell Res. 312, 2454 (2006)]. Briefly, mononuclear cells were seeded into the 8-Well Lab-Tek II Chamber Slide (Fisher Scientific) at $1 \times 10^5$ cells/ml, 0.5 ml/well in RPMI 1640 medium supplemented with 7% fetal bovine serum (Invitrogen, Carlsbad, Calif.), and incubated at 37° C., 8% CO2 conditions. To expand cells in a large scale, mononuclear cells were initially seeded in the 150×15 mm Style Petri dishes (Becton Dickinson Labware, Franklin Lakes, N.J.) at $1 \times 10^6$ cells/ml, 25 ml/dish in RPMI 1640 medium supplemented with 7% fetal bovine serum. To demonstrate PB-SC are different from monocyte/macrophage by the removal of monocytes, freshly isolated peripheral blood mononuclear cells (PBMC) were planted in Petri dishes. After overnight attachment, floated cells were collected and confirmed for CD14 by flow analysis and then replanted in new Petri dishes; while the attached monocytes were added fresh medium for continue culture.

Flow Analysis and Cell Sorting

Flow analysis was preformed as previously described (14). Cells were detached by incubation in 3.5% lidocaine hydrochloride (Sigma) with 0.5 mM EDTA for 5-8 minutes at room temperature to harvest cells [Y. Zhao, H. Wang, T. Mazzone. Exp Cell Res. 312, 2454 (2006)]. For single staining, isotype-matched IgG 1κ served as negative control for mouse monoclonal antibodies; normal rabbit IgG served as negative control for rabbit polyclonal antibody including CD117. For double stainings, cells were initially performed intracellular staining as previously described [Y. Zhao, H. Wang, T. Mazzone. Exp Cell Res. 312, 2454 (2006)]. Then, cells were staining with another primary antibody FITC-conjugated CD45. The isotypematched FITC-conjugated IgG (BD Pharmingen) served as negative control. After staining, cells were analyzed using a CyAn ADP (DakoCytomation) and Summit v4.2 software. For cell sorting, freshly isolated PBMC were stained with FITC-conjugated mouse antihuman CD14 monoclonal antibody (BD Pharmingen). The isotype-matched FITC-conjugated IgG served as negative control. After flow analysis and confirming high purity (>99.9%), CD14⁻ cell population was collected and then seeded in the 8-Well Lab-Tek II Chamber Slide at $1 \times 10^5$ cells/ml, 0.5 ml/well in RPMI 1640 medium supplemented with 7% fetal bovine serum, and incubated at 37° C., 8% CO2 conditions.

Immunocytochemistry

Immunostaining was performed as previously described with minor modifications [Y. Zhao, H. Wang, T. Mazzone. Exp Cell Res. 312, 2454 (2006)]. The cells were incubated for 20 minutes at room temperature with ImmunoPure Peroxidase Suppressor (Pierce, Rockford, Ill.) to block endogenous peroxidase activity. To block the non-specific staining, 2.5% horse serum (Vector Laboratories) is usually used to incubate with samples for 20 min at room temperature and always yield negative. After incubation with primary antibodies, cells were stained with ABC kit (Vector Laboratories, Burlingame, Calif.). For pancreatic slides, we counterstained with hematoxylin for 8-10 min after immunostaining. Cells were photographed with a Zeiss Axiocam Color Camera using Zeiss Axioskop Histology/Digital Fluorescence microscope.

Western Blot

Cells cultured in Petri dishes were washed with PBS and then solubilized with RIPA buffer (150 mM NaCl, 1.0% NP-40, 0.5% DOC, 0.1% SDS, 50 mM Tris (PH 8.0)) with a cocktail of protease inhibitors (Sigma). After forcing through a 21G needle for 5 times, cell lysate was centrifuged at 12,000×g for 10 min at 4° C. Proteins samples (20 μg each) were mixed with a loading buffer (50 mM Tris, 10% SDS, 10% glycerol, 10% 2 mercaptoethanol, 2 mg of bromphenol blue) in a volume ratio of 1:1, boiled, loaded, and separated by electrophoresis on 10% SDS gel. Human ES cell lysate served as positive control; PBMC served as additional control for PB-SC. The separated proteins were then transferred to a nitrocellulose membrane, blocked with 5% non-fat dry milk in TBST for 1 h and incubated with different antibodies: including mouse anti human Oct-4 (1:500) and rabbit anti-human antibodies (1:1,000) to Nanog, PDX-1, NeuroD, NKX6.1, PC-1 and PC-2, diluted in PBST for 1 h at room temperature. After washing, the blot was exposed to a horseradish peroxidase-conjugated secondary antibody (1:2,000; Pierce) in PBS-T. The immunocomplexes were visualized by the enhanced chemiluminescence (ECL, GE healthcare) method. Beta-actin served as an internal loading control.

In situ Hybridization

To examine expression of Oct-4 mRNA, Nanog mRNA, and insulin mRNA, we performed in situ hybridization as previously described [Y. Zhao, T. Mazzone. Exp Cell Res. 310, 311 (2005)]. In brief, cells were fixed with 4% cold formaldehyde at 4° C. for 15 minutes. After blocking the endogenous peroxidase with ImmunoPure Peroxidase Suppressor (Pierce, Rockford, Ill.), the cells were used for in situ hybridization following the protocols provided by GeneDetect.com Ltd (Bradenton, Fla.). The biotin-labeled oligonucleotide probes to human Oct-4 (5'-AAAGCGGCA- GATGGTCGTTTGGCTGAAT-3' (SEQ ID NO: 7), NM002701) and Nanog (5'-TGGCAGGAGAATTTG-GCTGGAACTGCAT-3' (SEQ ID NO: 8), NM 024865) antisenses were obtained from Sigma-Genosys. The biotin-labeled oligonucleotide probes to human insulin antisense, sense control, and poly d(T) control were obtained from GeneDetect.com Ltd. Cells were incubated with the probes in hybridization buffer (DakoCytomation, Carpinteria, Calif.) at dilution 1:100 (1 µg/ml), 37° C. for 16-18 hours. The signals were detected using the Tyramide Signal Amplification System for In Situ Hybridizations by following their protocols as provided in the kit (DakoCytomation, Carpinteria, Calif.). The cells were viewed using a 40× oil immersion objective under the Zeiss Axioskop Histology/Digital Fluorescence microscope (Hallbergmoos, Germany), and then photographed with a Zeiss Axiocam Color Camera (Hallbergmoos, Germany). To confirm human PB-SC migrated into mouse pancreatic islets, we initially performed immunostaining using human C-peptide antibody (1:2,000, Linco Research, ST. Charles, Mo.), and then performed fluorescence in situ hybridization (FISH) using the human CEP® X/Y DNA Probe Kit (Vysis, Des Plaines, Ill.), following the manufacturer's protocols.

Phagocytosis Assay

Phagocytosis of macrophages PB-SC were performed as previously described with minor modifications [D. M. Underhill, et al, Nature 401, 811 (1999)]. Macrophages served as positive control. To generate macrophages, monocytes were treated with M-CSF (50 ng/ml) as previously described [Y. Zhao, D. Glesne, E. Huberman, Proc Natl Acad Sci USA 100, 2426 (2003)]. Cells cultured in 8-Well Lab-Tek II Chamber Slide were incubated with 1 mg/ml of fluorescence labeled Zymosan A bioparticles (Molecular Probes Inc., Eugene, Oreg.) in 200 µl volume/well at 37° C., 8% CO2 conditions. After incubation for 4 h, cells were washed 3-5 times with PBS and then incubated with lyticase (100 U/ml) for 10 min to remove non-specific binding of Zymosan A bioparticles. Finally, the cells were fixed in 4% formaldehyde in PBS and mounted with Mounting Medium (Vector Laboratories, Burlingame, Calif.). The cells were viewed and photographed using Zeiss LSM 510 META confocal microscope equipped with a 25× water immersion objective (Carl Zeiss Inc.), with HeNe 633 nm laser beam filtered through LP650. Cells contained ≥20 Zymosan A bioparticles/cell were regarded as positive for phagocytosis.

Characterization of PB-SC

Immunostaining showed that >90% of cells displayed embryonic transcription factors Oct-4 and Nanog, which are related to the self renewal of embryonic stem cells [Orkin S H: Chipping away at the Embryonic Stem Cell Network. Cell 122: 828-830, 2005]. Western blot and in situ hybridization further confirmed their protein and mRNA expressions. Human embryonic stem (ES) cell lysate served as positive control; and freshly isolated peripheral blood mononuclear cells (PBMC) served as additional control. Phenotypic analysis showed that PB-SC highly expressed hematopoietic cell antigens including tetraspanin CD9, leukocyte common antigen CD45, and stem cell factor receptor CD117 (FIG. 1); around 60% of cells was positive for endothelial progenitor marker CD31; but PB-SC were negative for hematopoietic stem cell marker CD34, lymphocyte markers CD3, CD20, and CD90, monocyte/macrophage antigens CD11b/Mac-1 and CD14 (FIG. 1). Especially, high expression of CD45 indicates that PB-SC are hematopoietic (CD45$^+$) origin, not mesenchymal (CD45$^-$) cells circulating in peripheral blood [da Silva Meirelles L, Chagastelles P C, Nardi N B: Mesenchymal stem cells reside in virtually all post-natal organs and tissues. J Cell Sci. 119: 2204-2213, 2006]. FIG. 1 displays data from flow cytometry analysis of hematopoietic cell markers on PB-SC. Normal rabbit IgG served as negative for CD117 polyclonal antibody; the isotype-matched mouse IgG antibody served as negative control for other monoclonal antibodies. Data represent results from eight experiments with the similar results. Scale bar, 47 µm;

Additionally, western blot revealed weak expression of Oct-4 and Nanog in peripheral blood. To evaluate their percentage, we performed flow analysis using CD45 and transcription factors Oct-4 or Nanog as indicators. Results showed that 0.1±0.01% of mononuclear cells were positive for CD45$^+$ Oct-4$^+$, 1.9±0.02% of mononuclear cells were for CD45$^+$ Nanog$^+$. The above experiments were performed in 8 buffy coats, yielded similar results. Taken together, these results suggest that PB-SC may represent a unique cell population.

Attached cells in blood are usually regarded as "macrophages". However, PB-SC failed to express human monocyte/macrophage specific antigens [Y. Zhao, D. Glesne, E. Huberman, Proc Natl Acad Sci USA 100, 2426 (2003)] CD14 and CD11b/Mac-1 (FIG. 1). To distinguish PB-SC from monocytes/macrophages, we examined PB-SC for monocyte/macrophage-related phenotypes [Y. Zhao, D. Glesne, E. Huberman, Proc Natl Acad Sci USA 100, 2426 (2003)] such as human leukocyte antigens (HLA): HLA-DR, HLA-DQ, and HLA-ABC, along with costimulating molecules: CD40, CD80, and CD86. Compared with monocytes, PB-SC were negative for HLA-DR, CD40, and CD80 (FIG. 2A). Less than 10% of cells were positive for CD86 and HLA-DQ; strongly expressed HLA-ABC (usually expressed on all nucleated cells) (FIG. 2A). FIG. 2A depicts flow analysis data on immune response-associated phenotypes. Blood monocytes served as positive control (vertically dashed) for PB-SC (solid); Iostype-matched mouse IgG served as negative control (horizontal dashes). Compared with macrophages [Y. Zhao, D. Glesne, E. Huberman, Proc Natl Acad Sci USA 100, 2426 (2003)], functional analysis showed that >95% of macrophages presented powerful phagocytosis of Zymosan A bioparticles, however PB-SC were only around 30%. The macrophages were generated from macrophage colony-stimulating factor (M-CSF)-treated monocytes. To further substantiate PB-SC were different from monocytes/macrophages, we performed cell sorting. After removal of monocyte (CD14$^+$), PB-SC could still be generated from CD14$^-$ cell population of peripheral blood mononuclear cells. Immunostaining showed that they were double positive for PB-SC markers: CD45 and transcription factors Oct-4 or Nanog. The experiment was done with double immunostaining of cultured CD14$^-$ cell population after cell sorting. After culture for 10-14 days, cells stained with antibodies to Oct-4, Nanog, and CD45, along with DAPI nuclear staining. Cells were photographed using Zeiss LSM 510 META confocal microscope.

To exclude the possibility that CD14-dim monocytes may be escaped for sorting, we performed additional experiments to remove monocytes by using attachment. After culture for 2 months, macrophage number showed no significant changes; however PB-SC significantly increased in cell number (FIG. 2B). Phase-contrast images showed cell cultures after removal of attached monocytes and macrophages (Mono/Macro) (data not shown). Cell number represents mean (±SD) of four experiments. Based on the data, we calculated the doubling time of PB-SC was about 5.6 days. Thus, these results indicate generation of PB-SC is independent of monocytes.

Example 2

PB-SC Differentiate to Insulin-Producing Cells to Treat Hyperglycemia in a Diabetic Mammalian Subject Diabetes in NOD-scid male mice, aged 8-10 weeks, was induced with a single intraperitoneal injection of streptozotocin (STZ) (Sigma) 180 mg/kg of body weight, freshly dissolved in citrate buffer (pH=4.5). Blood glucose levels were evaluated daily between 9 and 11 A.M. under nonfasting conditions. Severe diabetes was confirmed by the presence of weight loss, polyuria, and nonfasting blood glucose levels >450 mg/dl for 2 consecutive days, and then used for transplantation, according to a protocol approved by the Animal Care Committee (ACC) of University of Illinois at Chicago. In brief, PBSC at dosage of 5 million cells/mouse in 0.5 ml physiological saline was injected into the peritoneal cavity by injection with 27-gauge needle, normally on day 3 following the injection of streptozotocin. The control mice were injected only with an equal volume of physiological saline. Blood glucose levels were monitored using an AccuChek glucose detector (Roche Diagnostics, Indianapolis, Ind.). To measure human C-peptide, blood samples were collected from the tail vein after transplantation. Blood human C-peptide level was detected by using an ultrasensitive human C-peptide enzyme-linked immunosorbent assay (ELISA) kit (Alpco Diagnostics, Windham, N.H.) following the manufacturer's protocols. This assay does not detect mouse C-peptide. After transplantation for 30 days, immunohistochemistry analyses were performed on pancreas, liver, spleen, kidney, and adipose tissue of peritoneal cavity in PB-SC-transplanted diabetic mice.

To evaluate potential of PB-SC differentiating to insulin-producing cells, we initially examined pancreatic islet β-cell development-associated transcription factors [Edlund H: Pancreatic organogenesis-developmental mechanisms and implications for therapy. *Nat Rev Genet* 3: 524-532, 2002], including PDX-1, NeuroD and NKX6.1. Western blot demonstrated that PB-SC strongly expressed NeuroD, PDX-1 (a well-known transcription factor essential for beta cell development), and NKX6.1 (that commits pancreatic progenitors to β cells) (data not shown). PB-SC also expressed prohormone convertase PC1 and PC2 (data not shown), which are usually presented in islet β cells and other cellular tissues associated with peptide synthesis [Zhu X, Orci L, Carroll R, Norrbom C, Ravazzola M, Steiner D F: Severe block in processing of proinsulin to insulin accompanied by elevation of des-64,65 proinsulin intermediates in islets of mice lacking prohormone convertase 1/3. *Proc Natl Acad Sci USA*. 99: 10299-10304, 2002]. Western blots for transcription factors including PDX-1, NeuroD, and NKX6.1, along with prohormone convertases PC-1 and PC-2 were performed using freshly isolated peripheral blood mononuclear cells (PBMC) served as controls.

Next, we tested insulin production. For determination of total cellular insulin content, insulin was extracted from cell pellet with acid ethanol (10% glacial acetic acid in absolute ethanol) overnight at 4° C., followed by cell sonication. Insulin and C-peptide levels were assayed respectively using human insulin and C-peptide ultrasensitive enzyme-linked immunosorbence assay (ELISA) kit (ALPCO, Windham, N.H.). Protein concentrations were determined using bicinchoninic acid protein assay system (Sigma) following manufacture's instruction.

Figures 3A, 3B:
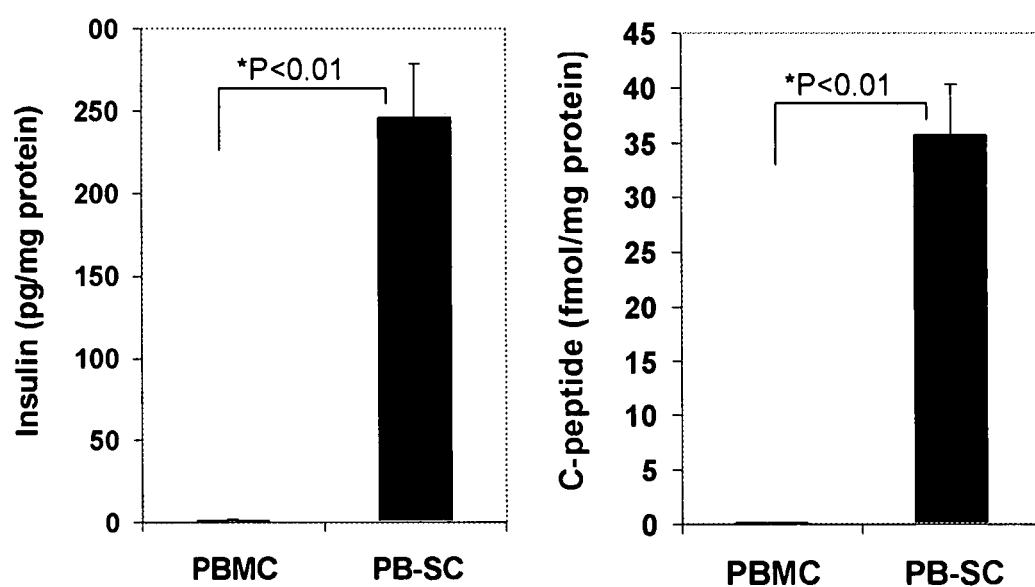
FIG. 3A is a bar graph showing the quantification of insulin levels per total cell protein by ELISA.
FIG. 3B is a bar graph showing the quantification of C-peptide levels per total cell protein by ELISA.

Immunostaining showed PB-SC were positive for insulin and C-peptide (a by-product of insulin production, images not shown). Their levels were evaluated by ELISA, around 246.07±32.88 pg/mg cell protein for insulin (FIG. 3A) and 35.76±4.5 fmol/mg cell protein for C-peptide (FIG. 3B). To exclude the possibility of uptaking from culture medium [Mousa S A, Shakibaei M, Sitte N, Schafer M, Stein C: Subcellular pathways of beta-endorphin synthesis, processing, and release from immunocytes in inflammatory pain. *Endocrinology*. 145: 1331-1341, 2004], insulin production was confirmed by in situ hybridization with a human insulin oligonucleotide probe for insulin mRNA (data not shown). Additionally, confocal analysis [Taylor N A, Van De Ven W J, Creemers J W: Curbing activation: proprotein convertases in homeostasis and pathology. *FASEB J*. 17: 1215-1227, 2003] showed insulin staining was colocalized in part (because PC1 and PC2 contribute not only for insulin synthesis, but also for other peptides) with convertase PC1 or PC2 (data not shown). Double immunostaining for insulin and PC-1 or PC-2 was performed. Colocalization was shown by merged images. Granule-like structures were identified Cells were examined and photographed using Zeiss LSM 510 confocal microscope [Zhu X, Orci L, Carroll R, Norrbom C, Ravazzola M, Steiner D F: Severe block in processing of proinsulin to insulin accompanied by elevation of des-64,65 proinsulin intermediates in islets of mice lacking prohormone convertase 1/3. *Proc Natl Acad Sci USA*. 99: 10299-10304, 2002].

Figure 3C:
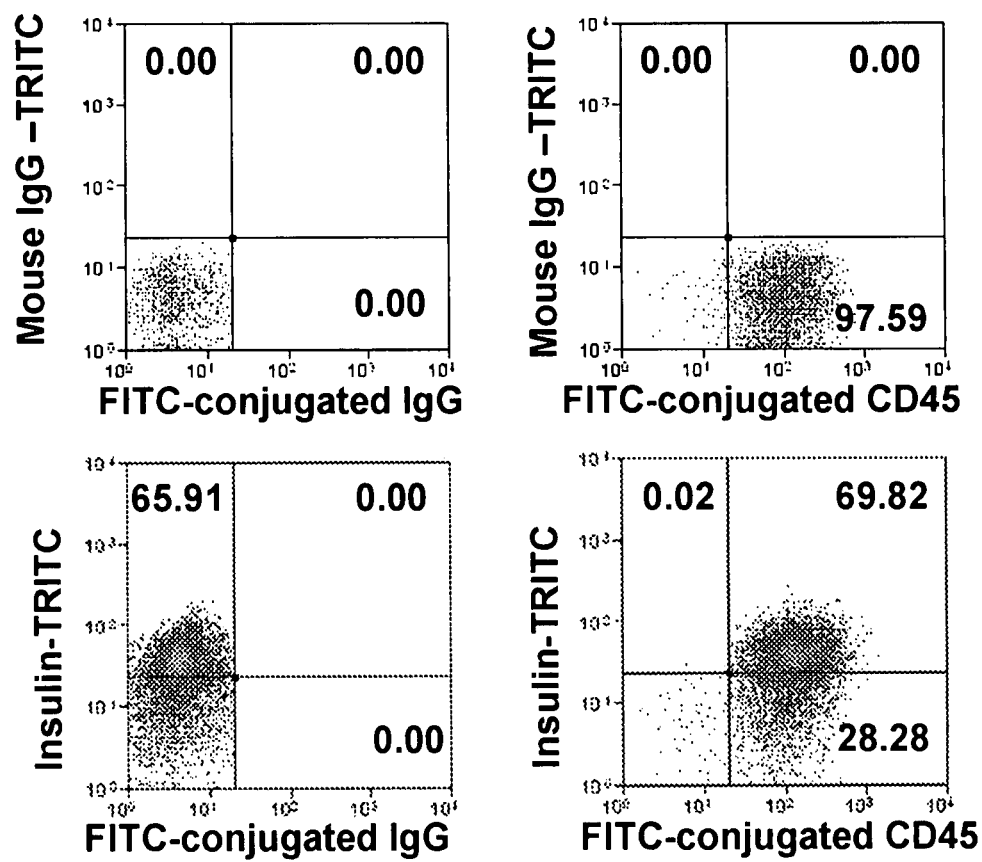
FIG. 3C depicts flow cytometry analysis on PB-SC for insulin and CD45.

Flow analysis showed that around 70% of PB-SC were double positive for $CD45^+$ $insulin^+$ (FIG. 3C). Altogether, these results strongly demonstrated that PB-SC can produce insulin. Flow analysis on PB-SC for insulin and CD45 was done using mouse IgG as negative control for insulin monoclonal antibody, and FITC-conjugated IgG as a negative for FITC-conjugated CD45.

To fully characterize PB-SC, we also examined other β-cell markers [Thorens B: GLUT2 in pancreatic and extra-pancreatic gluco-detection. *Mol Membr Biol*. 18: 265-273, 2001; Shibasaki T, Sunaga Y, Seino S. Integration of ATP, cAMP, and Ca2+ signals in insulin granule exocytosis. *Diabetes*. 53: S3:S59-62, 2004] including glucose transporter 2 (Glut-2), insulin-releasing-associated $K^+ATP$ channel protein suphonylurea receptor-1 (Sur-1), calcium channel subunit alpha 1C, glucokinase regulator protein (GCKR), as well as glucagon produced by pancreatic α cells. Immunostaining analysis for other beta cell-related markers and alpha cell-related glucagon showed that 70-80% of PB-SC displayed Glut-2, GCKR, and Sur1; >95% of cells showed alpha 1C; no expression of glucagon (data not shown). Data represent from four experiments with the similar results.

Figure 4:
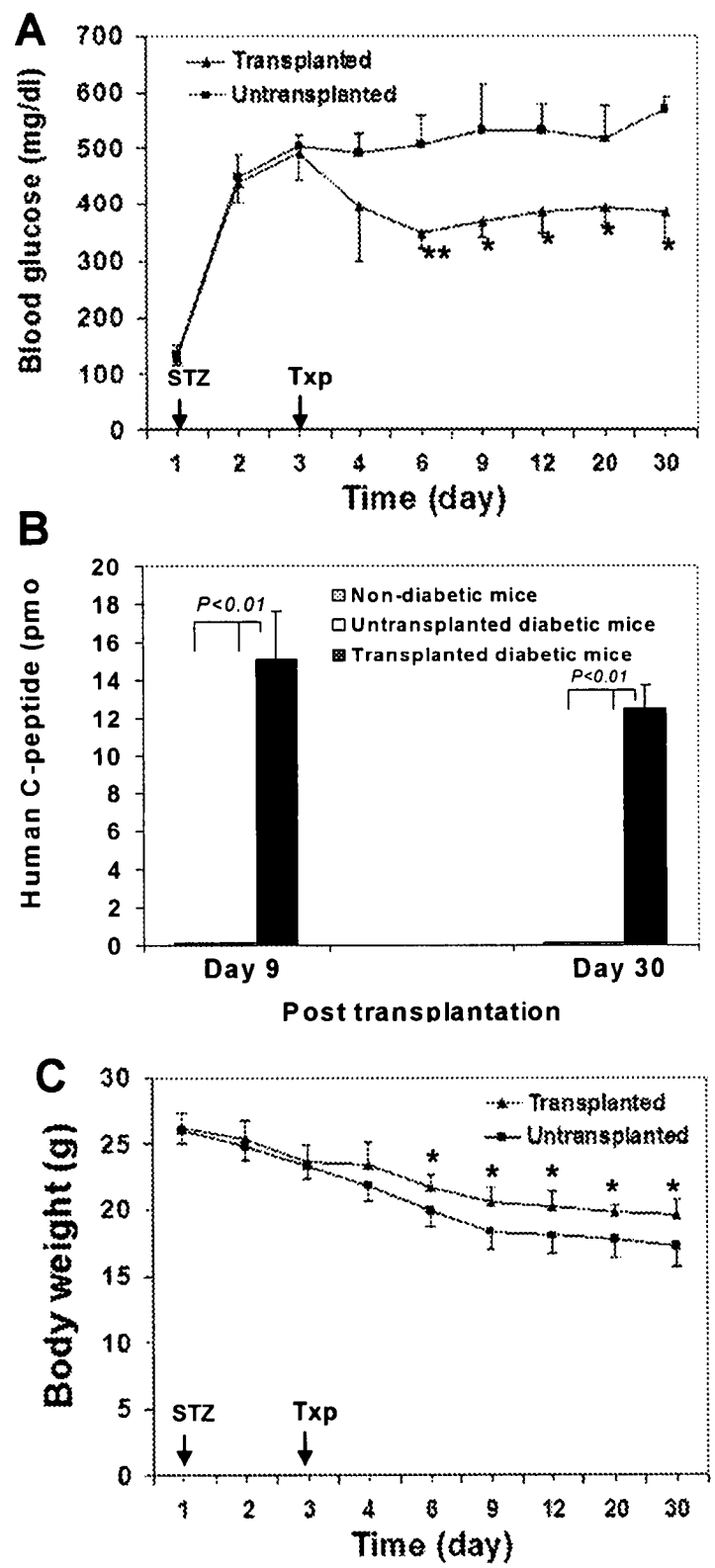
FIG. 4A is a graph of blood glucose levels post transplantation (Txp) of PB-SC in streptozotocin (STZ)-induced diabetic NOD-scid mice (5 million cells/mouse, i.p., n=5/group)
FIG. 4B is a bar graph comparing levels of human C-peptide by ELISA in mouse sera from non-diabetic mice, diabetic NOD-scid mice without transplantation, and diabetic NOD-scid mice post transplantation of PB-SC (n=3/group)
FIG. 4C is a graph of body weight in untranplanted streptozotocin (STZ)-induced diabetic NOD-scid mice and in streptozotocin (STZ)-induced diabetic NOD-scid mice post transplantation (Txp) of PB-SC, 5 million cells/mouse, i.p., n=5/group.

To further evaluate the potential of PB-SC give rise to functional insulin-producing cells, we therefore transplanted PB-SC into the streptozotocin (STZ)-induced diabetic NOD-scid mice. Compared with untransplanted diabetic mice, PB-SC transplantation could reduce about 20-30% of severe hyperglycemia (FIG. 4A) and increase body weight about 2.05±0.34 gram (p<0.05) (FIG. 4C). To demonstrate these glucose responses were associated with transplanted PB-SC, we utilized an assay that is specific for human C-peptide (does not recognize mouse C-peptide) to evaluate human insulin secretion [Zhao Y, Wang H, Mazzone T: Identification of stem cells from human umbilical cord blood with embryonic and hematopoietic characteristics. *Exp Cell Res*. 312: 2454-2464, 2006; Hori Y, Gu X, Xie X, Kim S K: Differentiation of insulin-producing cells from human neural progenitor cells. *PLoS Med*. 2: 347-356, 2005; Hayek A, Beattie G M: Experimental transplantation of human fetal and adult pancreatic islets. *J Clin Endocrinol Metab*. 82: 2471-2475, 1997; Zalzman M, Gupta S, Giri R K, Berkovich I, Sappal B S, Karnieli O, Zern M A, Fleischer N, Efrat S: Reversal of hyperglycemia in mice by using human expandable insulin-producing cells differentiated from fetal liver progenitor cells. *Proc Natl Acad Sci USA*. 100: 7253-7258, 2003]. Data showed that human C-peptide level was significantly increased after transplantation (FIG. 4B) (p<0.01). However, human C-peptide was undetectable in mouse sera of PB-SC-untransplanted diabetic mice and normal mice (FIG. 4B). Immunohistochemistry showed human C-peptide-positive cells were presented in pancreatic tissue of PB-SC-transplanted mice (data not shown). They entered into blood vessels inside of pancreas, distributed among exocrine tissues; notably, human C-peptide positive cells were found in residual mouse pancreatic islets. Thirty out of 46 pancreatic islets from 5 PB-SC-transplanted diabetic mice showed human C-peptide-positive cells; the number of positive cells ranged from 2-42 positive cells/islet. However, human C-peptide-positive cells were not observed in pancreatic islets (n=35) of the normal non-diabetic mice or PB-SC-untransplanted diabetic mice, as well as pancreatic ducts of diabetic mice. Double immunostaining showed human C-peptide-positive cells incorporated with glucagons-positive α-cells within mouse pancreatic islets. To confirm these human C-peptide-positive cells were derived from PB-SC, we performed fluorescence in situ hybridization (FISH) using human X/Y chromosome probes. Slides were photographed using Zeiss LSM 510 confocal microscope. Results revealed that these human C-peptide-positive cells displayed human chromosome X/X karyotyping. It indicates that they are human cells and PB-SC can migrate into pancreatic islets.

Figure 5:
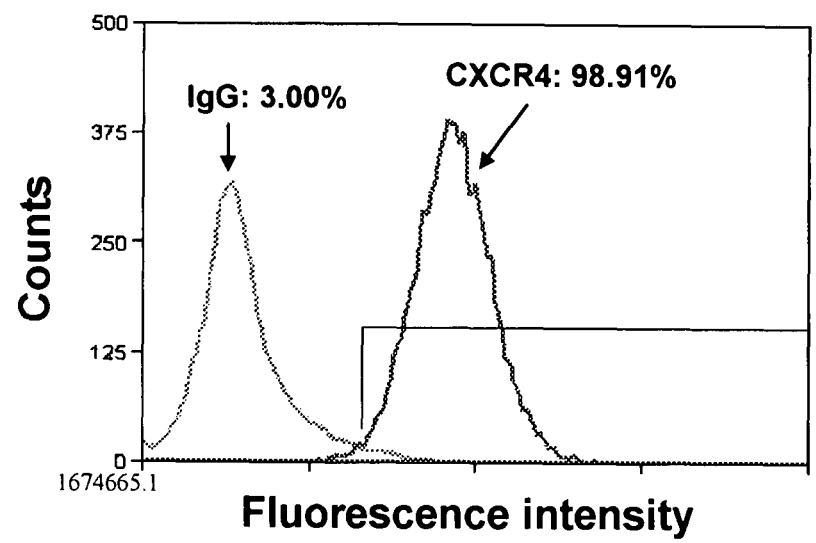
FIG. 5 is a graph showing the expression of the chemokine SDF-1 receptor CXCR4 on PB-SC by flow analysis compared to isotype-matched $IgG_1\kappa$ (negative control)

In addition, we performed immunohistochemistry analysis on other tissues of PB-SC-transplanted mice, e.g. liver, kidney, and adipose tissue of peritoneal cavity. These tissues failed to display human C-peptide staining. It suggests homing of PB-SC to pancreas is not a random process. To find the mechanism for PB-SC homing, we examined the expression of chemokine stromal cell-derived factor-1 (SDF-1) and its receptor CXCR4, which play an essential role in mediating hematopoietic stem cell homing [Lapidot T, Dar A, Kollet O: How do stem cells find their way home? *Blood* 106: 1901-1910, 2005]. Immunohistochemistry showed that the STZ-induced diabetic islets displayed SDF-1 (data not shown), which is consistent with previous report [Kayali A G, Van Gunst K, Campbell I L, Stotland A, Kritzik M, Liu G, Flodstrom-Tullberg M, Zhang Y Q, Sarvetnick N: The stromal cell-derived factor-1alpha/CXCR4 ligand-receptor axis is critical for progenitor survival and migration in the pancreas. *J Cell Biol.* 163: 859-869, 2003]; however normal pancreatic islets of non-diabetic mice, along with the liver, kidney, and adipocyte tissue of diabetic mice lacked expression of SDF-1. Rabbit IgG served as negative control; pancreatic slides from normal mice served as additional control. Notably, flow analysis demonstrated that PB-SC expressed its receptor CXCR4 (FIG. 5). Isotype-matched IgG$_1$κ served as negative control. Data represent one of three experiments with the similar results. It suggests that SDF-1 produced by diabetic islets may be a powerful chemoattractant for PB-SC homing.

Example 3

PB-SC Express Insulin Gene Transcription Factors

Figure 6A:
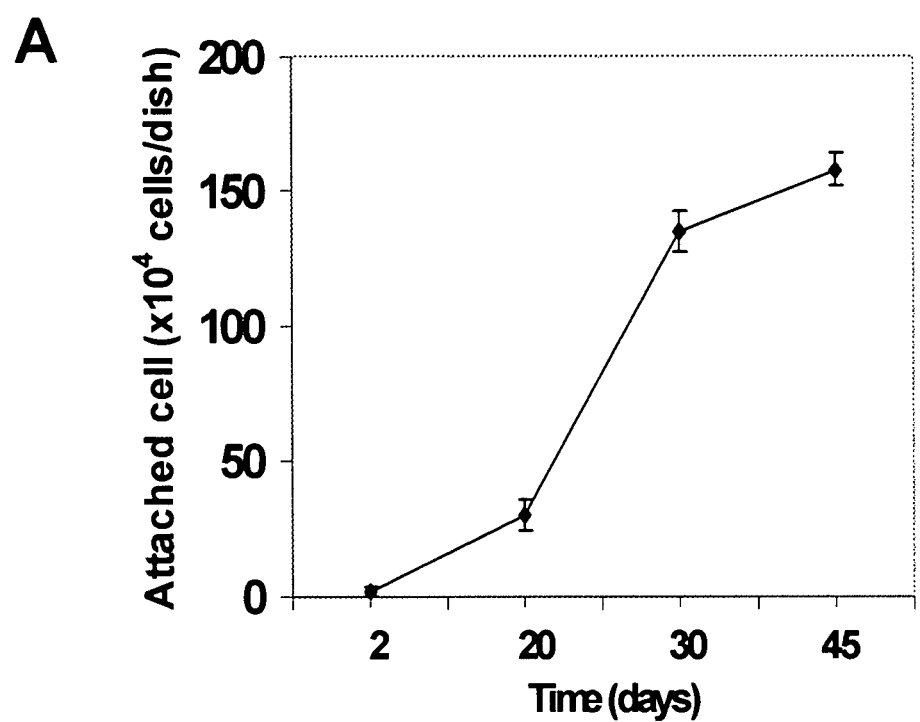
FIG. 6A is a graph showing PB-IPC proliferation showing that PB-IPC significantly increases in cell number over time.
Figure 6B:
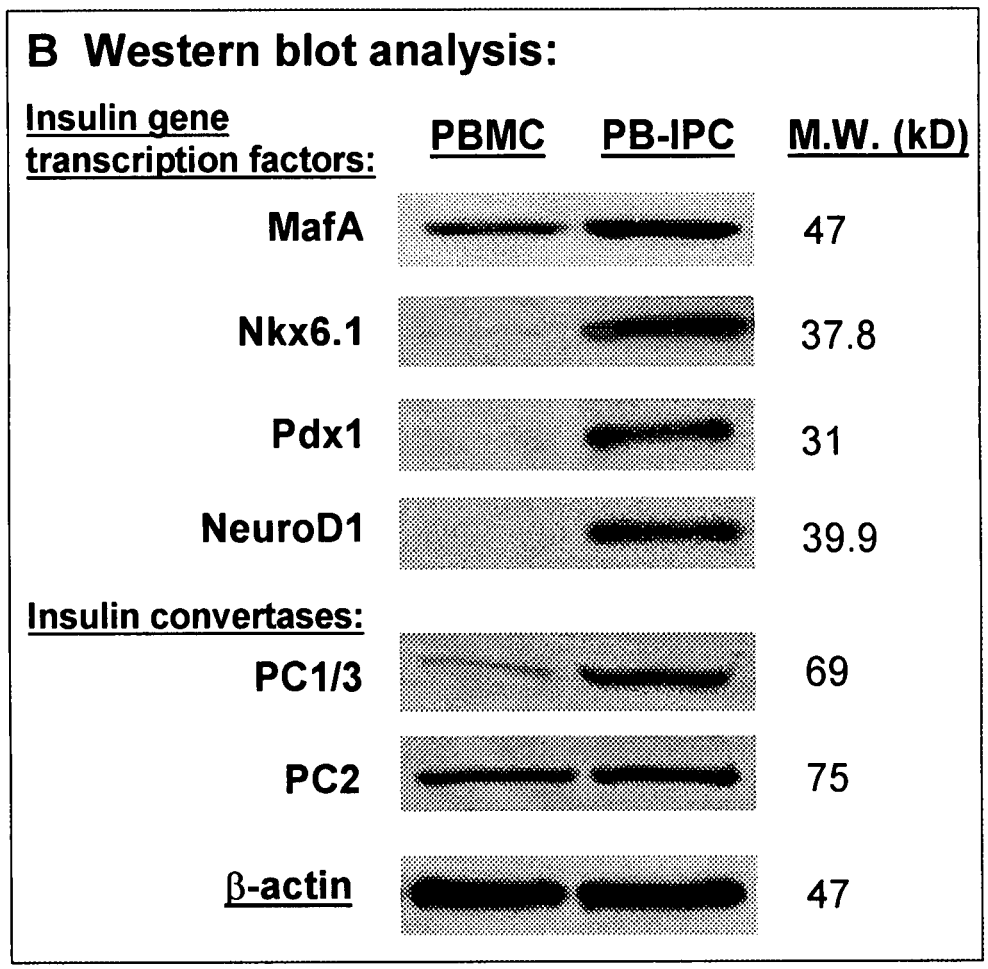
FIG. 6B depicts Western blot analysis showing that PB-IPC expressed increased levels of insulin gene transcription factors and insulin convertases in comparison with PBMC.

As shown in FIG. 6A, we observed that PB-IPC could proliferate and significantly increased in cell number. To evaluate the insulin-producing capability of the PB-IPC, we examined the insulin gene transcription factors such as the basic leucine zipper MafA, Pdx-1(pancreatic duodenal homeobox factor 1), NeuroD1 (neurogenic differentiation 1), HNF6 (hepatocyte nuclear factor 6, also known as Onecut1), Nkx6.1 (Nk homeobox gene), and Nkx2.2. We found that PB-IPC significantly expressed these transcription factors and increased their levels in comparison with PBMC (FIG. 6B); specifically for the β cell specific transcription factor MafA expression, immunostaining showed that 93±2% of PB-IPC strongly displayed nuclear staining for MafA (data not shown). MafA is a very specific insulin gene transcription factor for islet beta cells (Matsuoka T A, et al. *Proc Natl Acad Sci USA*. 2004; 101: 2930-2933); thus its expression indicates that the PB-IPC are progenitors of insulin-producing cells. Importantly, we observed that peripheral blood mononuclear cells (PBMC) also expressed MafA and Nkx6.1 at weak levels, but failed to show other transcription factors (FIG. 6B). It suggests that insulin-producing cells exist in the peripheral blood prior to our in vitro culture. To test this possibility, using quantitative real time PCR, we examined the above islet β cell-related transcription factors, the five kinds of pancreatic islet-produced endocrine hormones and the K(ATP) channel proteins (Table 1).

TABLE 1

Expression of pancreatic gene markers in the peripheral blood mononuclear cells (PBMC).

| Specific genes | PBMC Level ($\Delta C_T \pm$ SD) | Human islets Level ($\Delta C_T \pm$ SD) |
|---|---|---|
| Transcription factors: | | |
| MafA | +(14.70 ± 0.38) | +++(4.56 ± 0.35) |
| Nkx6.1 | +(19.79 ± 1.02) | +++(4.27 ± 0.32) |
| Pdx-1 | − | +++(5.26 ± 0.26) |
| Onecut1 | +(20.54 ± 1.88) | +++(8.78 ± 0.12) |
| NeuroD1 | − | +++(6.11 ± 0.22) |
| Nkx2.2 | − | +++(4.59 ± 0.16) |
| Pancreatic hormones: | | |
| Insulin | +(20.14 ± 1.76) | +++++(−4.67 ± 0.27) |
| Glucagon | − | ++++(−0.89 ± 0.20) |
| Pancreatic polypeptide | − | +++(3.00 ± 0.34) |
| Somatostatin | +(20.58 ± 0.60) | ++++(−2.89 ± 0.16) |
| Ghrelin | +(12.68 ± 0.16) | +++(4.87 ± 0.28) |
| K(ATP) channel proteins: | | |
| SUR1 | +(23.22 ± 0.80) | +++(5.10 ± 0.41) |
| Kir6.2 | +(16.59 ± 0.28) | +++(6.33 ± 0.34) |

Notes for Table 1:
1. Expression of different mRNAs was analyzed by quantitative real-time PCR, using the Mx3000p Quantitative PCR System (Stratagene, La Jolla, CA), under the following conditions: 95° C. for 15 min, 40 cycles of (95° C. for 30 s, 55° C. for 30 s, 72 ° C. for 30 s). The gene-specific RT$^2$ PCR Primer sets were purchased from SuperArray (Frederick, MD). The cDNA from freshly-isolated human islets served as positive control; peripheral blood mononuclear cells (PBMC) served as negative control.
2. Data represent their expression level ($\Delta C_T$ mean ± SD of three experiments) from non-detectable (−) to the high (+++++) after amplification for 40 cycles. For each sample, the difference between $C_t$ values ($\Delta C_T$) was calculated from the $C_t$ value of each gene and its β-actin internal control.
3. Production of pancreatic hormones: insulin is derived from β cells, glucagon from α cells, pancreatic polypeptide (PP) from PP cells, somatostatin from δ cells, ghrelin from ε cells.

Notably, we identified that PBMC expressed the genes of insulin, the insulin gene transcription factors (MafA, Nkx6.1, and HNF6), and the insulin secretion-related K(ATP) channel components (Sur1 and Kir6.2) (Table 1). These results confirmed that there are insulin-producing cells in peripheral blood. Interestingly, quantitative real time PCR also showed expressions of somatostatin (a δ cell product) and ghrelin (an ε cell product); however, other hormones (such as the α cell product glucagon and the PP cell product pancreatic polypeptide) and transcription factors (Pdx-1, NeuroD1, and Nkx2.2) were undetectable in comparison with positive control human islets (Table 1).

Thus, in the present disclosure, we identified and isolated insulin-producing cells from human peripheral blood. In adult peripheral blood, these cells can behave like islet β cell progenitors giving rise to the functional insulin-producing cells following transplantation into diabetic mice. It is easy to access, culture, expand, and differentiate, without any ethical issues and immune rejection; it is also safe without tumor formation. These findings open up new possibilities for autologous transplantation of these blood insulin-producing cells to treat diabetes.

Example 4

Blood Stem Cell-Treated Lymphocytes can Protect Against and Delay Diabetes Onset Blood-derived stem cells can regulate autoimmune lymphocytes and can be used to treat diabetes. The art recognized animal model of type 1 diabetes, the type 1 diabetic NOD mouse model, can be used to mimic type 1 diabetic patient. Lymphocytes can be isolated from spleens of NOD mice (6-7 weeks old) and then cocultured with human blood stem cells. After coculturing with embryonic-like stem cells for 4-5 days, the floated lymphocytes can be collected and administrated into the 6-week-old NOD mice (1-2 million lymphocytes/mouse, i.p., n=5). Physiological saline and non-cocultured mouse lymphocytes served as controls. Mice will be examined for protection against diabetes, including monitor blood glucose, body weight, glucose tolerance test, blood insulin test, and histological examinations. Embryonic-like stem cell-treated mouse lymphocytes could significantly delay and protect NOD mice for generation of diabetes. Glucose tolerance testing (IPGTT) could be done to evaluate the difference between the group of embryonic-like stem cell-treated lymphocytes and the group of normal mice.

ELISA can be used to examine mouse blood insulin levels both pre-and post IPGTT. Embryonic-like stem cell-treated lymphocytes may display normal insulin levels and response in response to high glucose challenge; while, control mice may display significantly lower levels of blood insulin levels and impaired responses. Histology examinations could be used to demonstrat that control mice displayed apparently insulitis in comparison with the group of embryonic-like stem cell-treated lymphocytes. Taken together, these experiments could confirm that administration of embryonic-like stem cell-treated lymphocytes could significantly protect diabetes onset in type 1 diabetes.

Example 5

Blood Stem Cell-Derived Insulin-Producing Cells Suppress the Proliferation of Autoimmune Lymphocytes As demonstrated in the Examples, PB-SC can differentiate into insulin-producing cells. Controlling autoimmune lymphocytes can be used to treat or ameliorate or reduce the risk of developing type 1 diabetes, because autoimmune lymphocytes can destroy not only the islet beta cells but also the stem cell-derived insulin-producing cells. This example establishes the efficacy of blood stem cell-derived insulin-producing cells to control those autoimmune lymphocytes without the addition of other demanding strategies.

We (Zhao Y, et al. Immunology Letters, 108:78, 2007.) showed that programmed death receptor-1 ligand 1 (PD-L1) expressed on CB-SC membrane, together with a soluble factor nitric oxide (NO) released by PHA-stimulated CB-SC, not prostaglandin E2 (PGE2) and transforming growth factor-β1 (TGF-β1), mainly contributed to the T cell suppression induced by CB-SC, as demonstrated by blocking experiments with a nitric oxide synthase inhibitor (N-omega-nitro-L-arginine, L-NNA) and a neutralizing antibody to PD-L1. To evaluate the therapeutic potential of blood stem cell-derived insulin-producing cells, we examined expressions of inducible nitric oxide synthase (iNOS) and PD-L1 in the adult human peripheral blood-derived insulin-producing cells after treatment with 10 nM Exendin4+10 ng/ml GM-CSF+25 mM glucose in 7% FBS-DMEM culture medium for 3-5 days. Results demonstrated that they expressed iNOS at high level (data not shown); low percentages of cells (5-10%) were also positive for PD-L1. Thus, the insulin-producing cells can regulate the diabetic lymphocytes through the soluble factors, such as NO, and also through cell-cell contact, such as through increased expression of programmed death receptor-1 ligand expressed on the embryonic-like stem cells that can suppress lymphocytes through the interaction with PDL receptor on lymphocytes.

Notably, we found that human blood stem cells and/or blood stem cell-derived insulin-producing cells expressed carboxypeptidase M (CPM) and carboxypeptidase E (CPE), as demonstrated by real time PCR. The expression of CPM was further confirmed by immunostaining using the monoclonal antibody. Both carboxypeptidase M and carboxypeptidase E can hydrolyze the carboxy-terminal (C-terminal) peptide bond of proteins and peptides by releasing the last amino acid (argine) of the chain. For example in islet beta cells, after cleavage of proinsulin by protein convertases PC1/3 or PC2, the remaining COOH-terminal basic residues are removed from the B-chain ($Arg^{31}$-$Arg^{32}$) and C-peptide ($Lys^{64}$-$Arg^{65}$) by carboxypeptidase E (CPE) resulting in the formation of mature insulin and C-peptide (Docherty K, Hutton J C 1983 *Carboxypeptidase activity in the insulin secretory granule. FEBS Lett* 162:137-141). The released argine can serve as the substrate for iNOS and contribute to NO production (Hadkar V, et al. *Am J Physiol Lung Cell Mol Physiol.* 2004 July; 287(1):L35-45).

Figure 7:
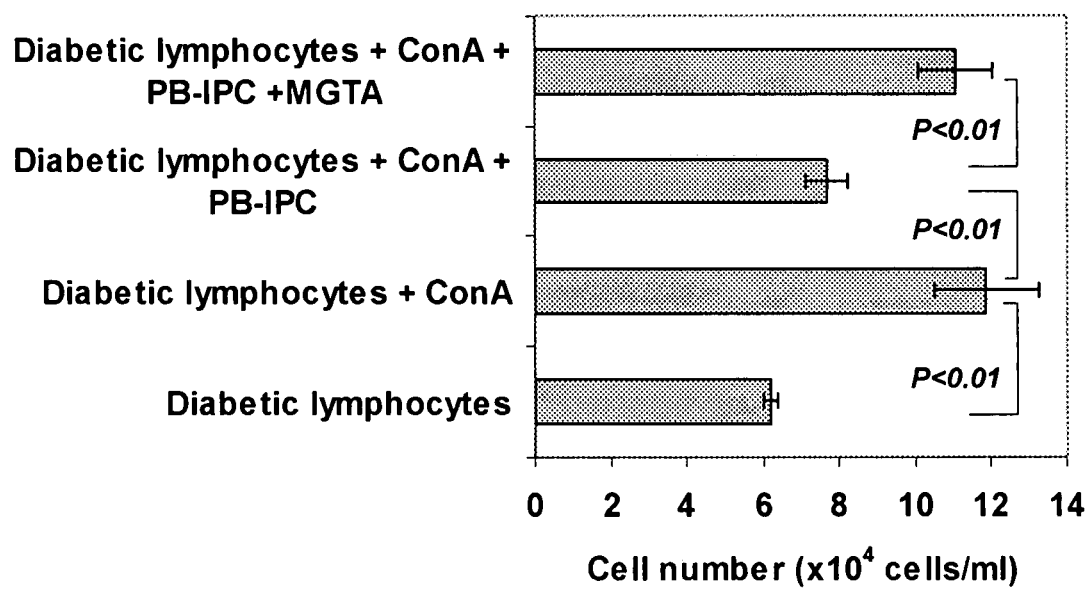
FIG. 7 is a bar graph showing lymphocyte proliferation demonstrating that adult human peripheral blood-derived insulin-producing cells (PB-IPC) can inhibit the proliferation of ConA-stimulated lymphocytes, and reverted in the presence of the specific carboxypeptidase inhibitor, carboxypeptidase inhibitor 2-mercaptomethyl-3-guanidinoethylthiopropanoic acid (MGTA, 10 μM)

We demonstrate that carboxypeptidase-derived NO can contribute to the lymphocyte suppression of blood stem cell-derived insulin-producing cells. The specific carboxypeptidase inhibitor, carboxypeptidase inhibitor 2-mercaptomethyl-3-guanidinoethylthiopropanoic acid (MGTA, 10 μM) was applied to block carboxypeptidase. First, adult human peripheral blood-derived insulin-producing cells were differentiated by treatment with 10 nM Exendin4+10 ng/ml GM-CSF+25 mM glucose in 7% FBS-DMEM culture medium for 3-5 days. Second, autoimmune lymphocytes were isolated form the diabetic NOD mouse and then cocultured with these adult human peripheral blood-derived insulin-producing cells in the presence MGTA. The mouse lymphocyte mitogen concanavalin A (ConA) was used to stimulate the proliferation of lymphocytes. Results demonstrated that the adult human peripheral blood-derived insulin-producing cells could inhibit the proliferation of ConA-stimulated lymphocytes ($p<0.01$); and administration of carboxypeptidase inhibitor MGTA could completely revert their inhibition ($p<0.01$) (FIG. 7).

Example 6

PB-SC Display Embryonic Stem Cell Markers and Blood Lineage Markers

Figure 8A:
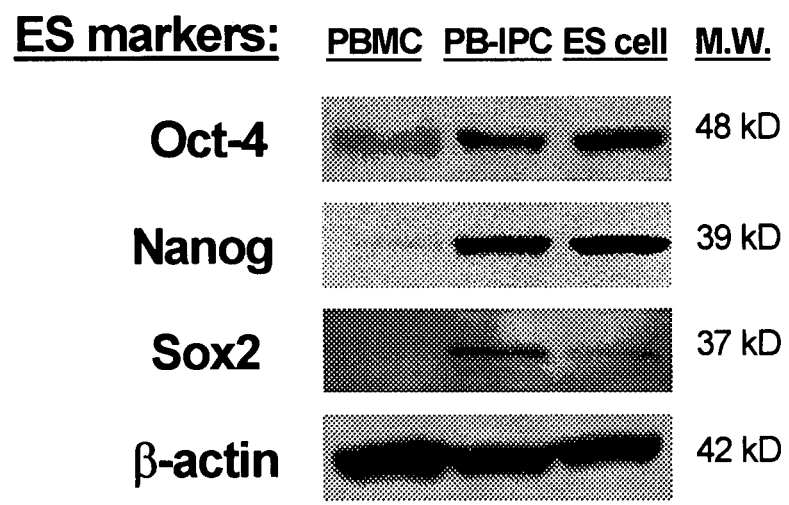
FIG. 8A depicts Western blot analysis showing that PB-SC display the ES cell-specific markers Oct-4, Nanog, and Sox2.

Western blot showed that PB-SC displayed ES cell-specific markers, e.g. embryonic transcription factors Oct-4, Nanog, and Sox2 (FIG. 8A). Additionally, real time PCR was performed by using embryonic stem (ES) cell-related genes to show which genes are expressed in the PB-SC (FIG. 8B), e.g., Zinc finger and SCAN domain containing 10 (ZNF206, also named ZSCAN10) (Access no. NM_032805.1, NP_116194.1), Zic family member 3 heterotaxy 1 (ZIC3) (Accession No. NM_003413), Zic family member 2 (ZIC2) (Accession No. NM_007129), Growth associated protein 43 (GAP43) (Accession No. NM_002045), PR domain containing 14 (PRDM14) (Accession No. NM_024504), Protein tyrosine phosphatase receptor-type, Z polypeptide 1 (PTPRZ1) (Accession No. NM_002851), Podocalyxin-like (PODXL) (Accession No. NM_005397), Polyhomeotic homolog 1 (PHC1) (Accession No. NM_004426), and Zinc finger protein 589 (ZNF589) (Accession No. NP_057173.1).

Figure 8B:
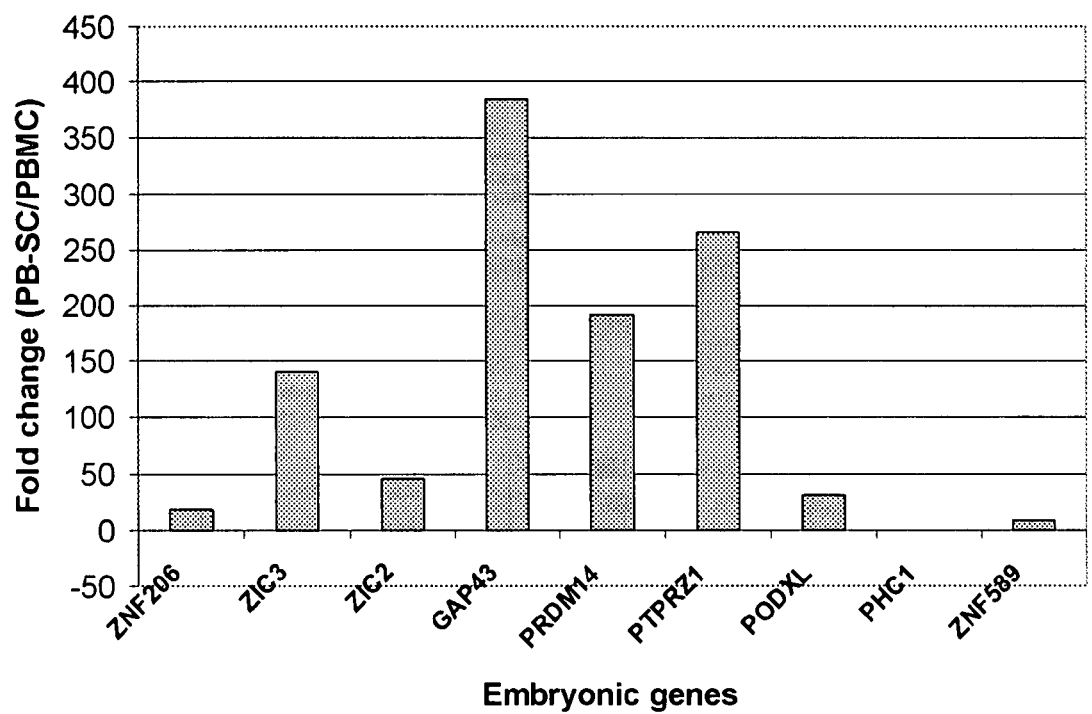
FIG. 8B depicts results from real time PCR showing that embryonic genes are expressed in PB-SC.
Figure 8C:
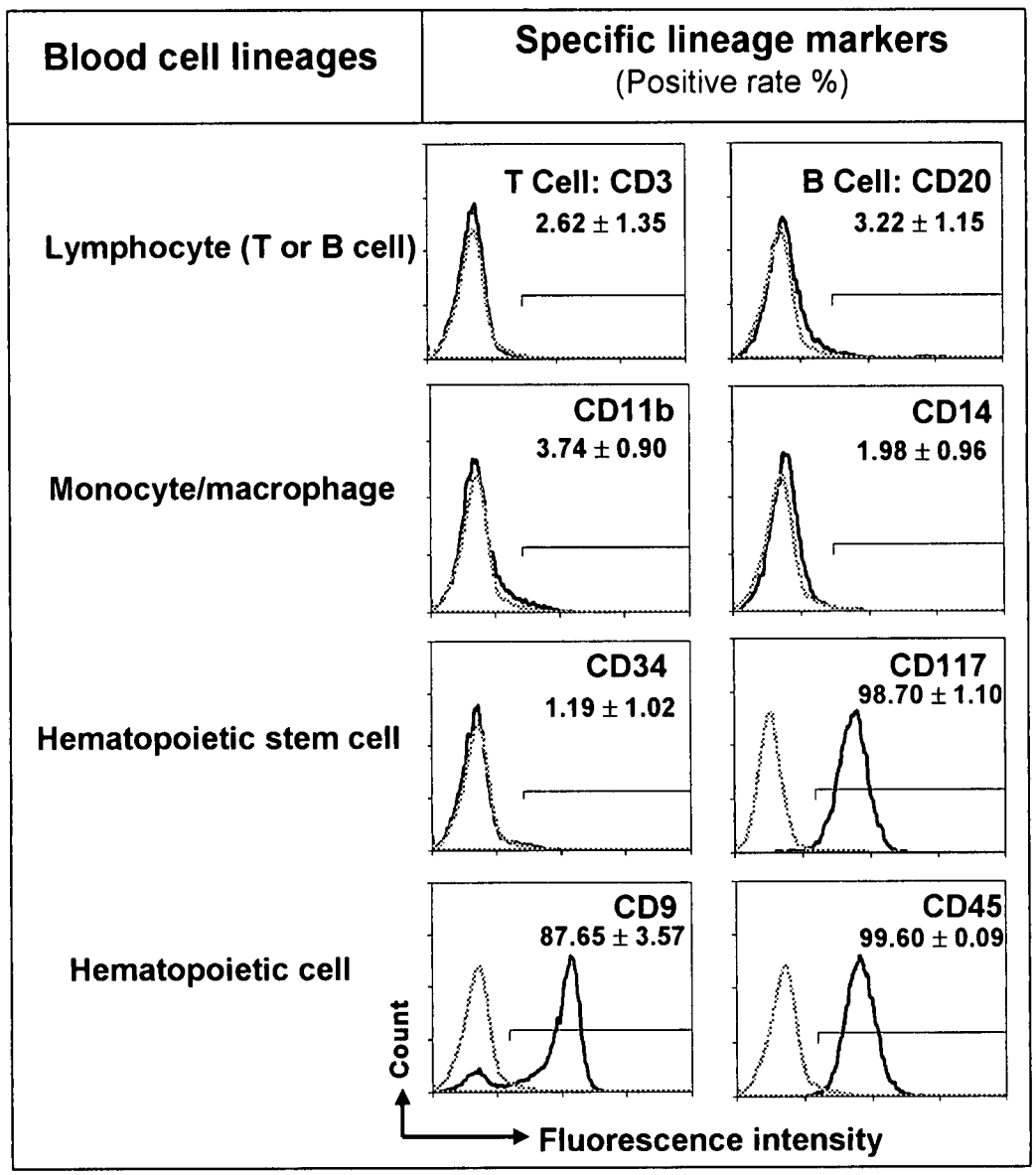
FIG. 8C depicts flow analysis data of PB-IPC showing that the PB-IPC are positive for the specific lineage markers of CD45 (hematopoietic cells), CD9 (hematopoietic cells), and CD117 (hematopoietic stem cells); and lymphocyte markers CD3 and CD20, monocyte/macrophage markers CD11b and CD14, and hematopoietic stem cell marker CD34.

This experiment demonstrated that PB-SC displayed embryonic characteristics. Phenotypic analysis was also done to examiner which blood lineage cell markers are displayed on PB-SC. Flow cytometry showed that these PB-SC cells were positive for CD45 (Accession No. P08575, NM002838) (hematopoietic cells), CD9 (GenBank Accession Nos. NM_001769 and M38690) (hematopoietic cells), and CD117 (GenBank Accession No. P10721, NM_000222) (hematopoietic stem cells), and/or chemokine (C-X-C motif) receptor 4 (CXCR4) (GenBank Accession No. AF005058) (FIG. 8B and FIG. 5). Therefore, these cells can also be isolated by cell sorting using these surface molecules.

Example 6

PB-SC can Differentiate into Different Cell Types

Therefore, the embryonic-like cells of the present invention can differentiate into other lineages including, but not limited to, beta cells, pancreatic cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells. In some embodiments, exposure to different inducers can induce differentiation of the embryonic-like cells. This example shows that that the PB-SC cells display multiple potential of differentiation.

(i) Differentiation of PB-IPC into Beta Cell-like Insulin-producing Cells.

PB-SC cells were treated with 10 nM Exendin4+10 ng/ml GM-CSF+25 mM glucose in 7% FBS-DMEM culture medium for 3-5 days. Immunostainings and real time PCR analysis showed that beta cell-related markers (e.g., insulin and C-peptide production, expressions of Glut-2 and $K_{ATP}$ channel protein Sur1 and Kir6.2) were significantly upregulated in comparison with the untreated cells. Notably, these cells could form an islet-like structure (data not shown). Immunostaining with insulin monoclonal antibody demonstrated that these islet-like cell clusters were positive for insulin. Taken together, these data indicate that PB-IPC differentiate into the beta cell-like cells after treatment with these inducers.

(ii) Differentiation into the Neuronal-like Cells.

PB-SC cells were treated with nerve growth factor (NGF, 100 ng/ml) for 10-14 days. Approximately 15% of these cell differentiated into neuronal-like cells with elongated cells processes forming net works; immunostainings with neuronal markers showed that they were positive for synaptophysin (Synap), γ-aminobutyric acid (GABA) and glutamate decarboxylase65/67 (GAD). This data indicates that the embryonic-like stem cells can turn into neuronal cells.

(iii) Differentiation into Cardiomyocyte-like Cells.

To further evaluate the differentiation potential of the PB-SC, we evaluated the cells for the presence of cardiomyocyte-related markers. Immunostaining results showed that these embryonic-like stem cells can spontaneously differentiate into cardiomyocyte-like cells, as demonstrated by expression of cardiomyocyte-specific transcription factor NKX2.5, structure proteins actinin, contractile-related tropomyosin and troponin I, and the cardiac hormone atrial natriuretic peptide (ANP) (data not shown). Following treatment with 5-Aza-2'-deoxycytidine for 48 h could increase the expression of structure protein desmin. Further optimization with inducers like 5-Aza-2'-deoxycytidine, retinoic acid (RA), and/or dimethyl sulfoxide (DMSO) can improve their differentiation toward cardiomyocyte.

(iv) Differentiation into Megakaryocyte-like Cells.

PB-SC cells were treated with thrombopoietin (TPO, 10 ng/ml) for 10-14 days and then performed immunofluorescence staining. Results showed that approximately 8% of cells differentiated into cells with the morphology of megakaryocytes and were positive for megakaryocyte-specific surface marker CD41b and also displayed polyploid nuclear formation. This data indicates that the embryonic-like stem cells of the present invention can differentiate into the megakaryocyte While the present invention has been described in terms of specific methods and compositions, it is understood that variations and modifications will occur to those skilled in the art upon consideration of the present invention. Those skilled in the art will appreciate, or be able to ascertain using no more than routine experimentation, further features and advantages of the invention based on the above-described embodiments. The practice of the present invention will employ and incorporate, unless otherwise indicated, conventional techniques of cell biology, cell culture, molecular biology, microbiology, genetic engineering, and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. Accordingly, the invention is not to be limited by what has been particularly shown and described. All publications and references are herein expressly incorporated by reference in their entirety.

The invention claimed is:

1. A method of harvesting embryonic-like stem cells from peripheral blood comprising:
   extracting peripheral blood comprising peripheral blood mononuclear cells (PBMCs);
   culturing the PBMCs in growth medium within a vessel having at least one hydrophobic surface, such that the PBMCs revert to embryonic-like stem cells and adhere to the hydrophobic surface;
   obtaining an embryonic-like stem cell population from the PBMCs that are attached to the hydrophobic surface; and
   isolating embryonic-like stem cells having characteristics comprising positive for CD45 marker and at least one of Oct-4, Nanog, Sox-2, and CD117 marker, negative for CD14 and CD34 markers and at least one of CD3, CD20, CD11c, and CD 11b/Mac-1 marker.

2. The method of claim 1, wherein the step of culturing further comprises seeding said PBMC's on a hydrophobic surface with a net positive charge.

3. The method of claim 2, wherein said surface is selected from the group consisting of polystyrene and glass.

4. The method of claim 1, wherein the step of isolating the embryonic-like stem cells further comprises selecting cells that are also positive for Octamer-binding transcription factor 4 (Oct-4), Nanog homeobox (Nanog), and SRY (sex determining region Y)-box 2 (Sox-2), and also negative for CD11b/Mac-1.

5. The method of claim 1, wherein the step of isolating the embryonic-like stem cells further comprises isolating a substantially homogeneous population of embryonic-like stem cells.

6. The method of claim 2, wherein the step of isolating said cells attached to the surface further comprises incubating the cells with a solution comprising lidocaine hydrochloride.

7. The method of claim 6, wherein the solution further comprises ethylenediamine tetraacetic acid (EDTA).

8. The method of claim 1, wherein the growth medium comprises RPMI 1640 medium and fetal bovine serum.

9. The method of claim 1, wherein the step of extracting peripheral blood further comprises removing red cells from peripheral blood to obtain PBMCs.

10. A method of obtaining a population of differentiated cells, the method comprising directing cell differentiation of the isolated embryonic-like stem cells of claim 1 by incubating the embryonic-like stem cells with an inducer, wherein said inducer directs maturation of the embryonic-like stem cells into a defined population of cells.

11. The method of claim 10, wherein the inducer is selected from the group consisting of Exendin-4, granulocyte monocyte colony stimulating factor (GM-CSF), granulocyte-macrophage colony-stimulating, nerve growth factor (NGF), 5-Aza-2'-deoxycytidine, retinoic acid (RA), dimethyl sulfoxide (DMSO), thrombopoietin, hepatocyte growth factor (HGF), vascular endothelial growth factor isoform165 (VEGF165), epidermal growth factor (EGF), erythropoietin (EPO), interleukin-2 (IL-2), IL-5, IL-7, IL-18, interferon-gamma, granulocyte-macrophage colony-stimulating factor (GM-CSF), macrophage colony-stimulating factor (M-CSF), phorbol 12-myristate 13-acetate (PMA), lipopolysaccharide (LPS), granulocyte colony-stimulating factor (G-CSF), all trans-retinoic acid (ATRA), vitaminD3, bone morphogenetic proteins (BMPs), brain derived neurotrophic factor (BDNF), glial derived neurotrophic factor (GDNF), growth factors, fibroblast growth factor (FGF), transforming growth factors (TGF), ciliary neurotrophic factor (CNTF), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, silencers, SHC(SRC-homology-2-domain-containing transforming protein), neuroproteins, proteoglycans, glycoproteins, neural adhesion molecules, and other cell-signalling molecules and mixtures, thereof.

12. The method of claim 10, wherein the defined population of cells has properties of cells selected from the group consisting of beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells.

13. An isolated population of cells consisting essentially of embryonic-like stem cells harvested from human peripheral blood comprising:
   a positive marker for CD45 and at least one of Oct-4, Nanog, and Sox-2; and
   a negative marker for CD34 and CD14 and at least one of CD3, CD20, CD 11c, and CD11b/Mac-1;

wherein the isolated population of embryonic-like stem cells are adherent to hydrophobic surfaces.

14. The isolated population of embryonic-like stem cells of claim 13, wherein said cells are capable of differentiating into insulin-producing cells.

15. The isolated population of embryonic-like stem cells of claim 14, wherein the cells are capable of differentiating into insulin-producing cells that express at least one insulin gene transcription factor.

16. The isolated population of embryonic-like stem cells of claim 15, wherein at least one insulin gene transcription factor is selected from the group consisting of leucine zipper MafA, Pdx-1 (pancreatic duodenal homeobox factor 1), NeuroD1 (neurogenic differentiation 1), HNF6 (hepatocyte nuclear factor 6), Nkx6.1 (Nk homeobox gene), and Nkx2.2.

17. The isolated population of embryonic-like stem cells of claim 14, wherein the cells further comprises at least one of the following embryonic genes selected from the group consisting of Zinc finger protein 206 (ZNF206), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), and Zinc finger protein 589 (ZNF589).

18. A method of suppressing activity of lymphocytes, comprising:
   obtaining the embryonic-like stem cells according to claim 1; and
   co-culturing a first population of cells comprising the embryonic-like stem cells with a second population of cells comprising the lymphocytes, wherein the embryonic-like stem cells interact with the lymphocytes to suppress the activity of the lymphocytes.

19. The method of claim 18, wherein said lymphocytes are allogeneic lymphocytes or autologous lymphocytes to the embryonic-like stem cells.

20. The method of claim 18, wherein the method further comprises isolating the second population of cells comprising the suppressed lymphocytes.

21. The method of claim 18, wherein the step of co-culturing further comprises decreasing intracellular IL-10 levels or increasing expression of CD69 on the suppressed lymphocytes.

22. The method of claim 18, wherein the embryonic-like stem cells release nitric oxide (NO).

23. The method of claim 20, wherein the method further comprises administering the isolated cells to a subject to ameliorate or delay onset of type I diabetes.

24. A method of treating diabetes in a mammalian subject in need thereof, comprising
   obtaining the embryonic-like stem cells according to claim 1; and
   administering said cells to the subject in an amount effective to treat diabetes.

25. The method of claim 24, wherein the cells are differentiated into insulin-producing cells.

26. The method of claim 24, wherein said administering step is carried out by intraveneous or intraarterial injection.

27. The method of claim 24, wherein said diabetes is insulin-dependent diabetes.

28. The method of claim 24, wherein said cells are administered into the pancreas of said subject.

29. The method of claim 24, wherein said peripheral blood is obtained from the subject.

30. The method of claim 24, wherein said peripheral blood is obtained from an allogenic source to the subject.

31. The method of claim 24, wherein said cells are encapsulated in an insulin-permeable capsule.

32. The method of claim 24, wherein said step of obtaining embryonic-like stem cells further comprises
   isolating the embryonic-like stem cells that are positive for CD45 and CD117 markers and at least one of Oct-4, Nanog, and Sox-2, and negative for CD14 and CD34 markers and at least one of CD3, CD20, CD11c, and CD11b/Mac-1 marker.

33. The method of claim 24, wherein the step of culturing further comprises seeding said PBMC's on a surface with a net positive charge.

34. The method of claim 24, wherein the step of isolating the embryonic-like stem cells comprises isolating said cells attached to the surface.

35. The method of claim 24, further comprises increasing insulin production in the subject.

\* \* \* \* \*